US011800994B2

(12) United States Patent
Herbst et al.

(10) Patent No.: US 11,800,994 B2
(45) Date of Patent: Oct. 31, 2023

(54) PATIENT SUPPORT APPARATUS WITH IMPROVED USER INTERFACE

(71) Applicant: Stryker Corporation, Kalamzoo, MI (US)

(72) Inventors: Cory Patrick Herbst, Shelbyville, MI (US); Kurosh Nahavandi, Portage, MI (US); David Buick, Portage, MI (US); Placide Nibakuze, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 27 days.

(21) Appl. No.: 17/623,406

(22) PCT Filed: Jun. 25, 2020

(86) PCT No.: PCT/US2020/039481
§ 371 (c)(1),
(2) Date: Dec. 28, 2021

(87) PCT Pub. No.: WO2020/264069
PCT Pub. Date: Dec. 30, 2020

(65) Prior Publication Data
US 2022/0346671 A1 Nov. 3, 2022

Related U.S. Application Data

(60) Provisional application No. 62/868,240, filed on Jun. 28, 2019.

(51) Int. Cl.
*A61B 5/11* (2006.01)
*A61G 7/002* (2006.01)
*A61B 5/00* (2006.01)

(52) U.S. Cl.
CPC ............ *A61B 5/1115* (2013.01); *A61G 7/002* (2013.01); *A61B 5/6891* (2013.01)

(58) Field of Classification Search
CPC ........... A61B 5/00; A61B 5/11; A61B 5/1115; A61B 5/1117; A61B 5/7267;
(Continued)

(56) References Cited

U.S. PATENT DOCUMENTS

2006/0028350 A1* 2/2006 Bhai ..................... A61B 5/1115
177/144
2016/0058641 A1 3/2016 Moutafis et al.
(Continued)

FOREIGN PATENT DOCUMENTS

WO 2019073389 4/2019
WO 2020132194 6/2020

OTHER PUBLICATIONS

NPL Search (Mar. 22, 2022).*
(Continued)

*Primary Examiner* — Van T Trieu
(74) *Attorney, Agent, or Firm* — Warner Norcross + Judd LLP

(57) ABSTRACT

A patient support apparatus, such as a bed, cot, stretcher, or the like, includes an exit detection system and/or a monitoring system that monitors a set of conditions of the patient support apparatus. A user interface of the exit detection system includes a first navigation control for navigating to a control screen for the exit detection system and a second navigation control for navigating to a control screen for the monitoring system. Each navigation control also functions as an automatic arming control, thereby causing the respective exit detection system and monitoring system to be armed. In this manner, a single touch of a navigation control implements the dual function of automatically arming the
(Continued)

corresponding system and taking the user to a control screen for the corresponding system. The automatically armed system is armed using one or more preset settings or one or more settings customized to a particular patient.

18 Claims, 12 Drawing Sheets

(58) Field of Classification Search
CPC ....... A61B 5/7275; A61B 5/747; A61B 5/746; G08B 21/00; G08B 21/04; G08B 21/0461; A61G 1/00; A61G 1/04; A61G 7/00; A61G 7/002; A61G 7/015; A61G 7/05; A61G 7/0507; A61G 13/10
See application file for complete search history.

(56) References Cited

U.S. PATENT DOCUMENTS

| | | | |
|---|---|---|---|
| 2016/0106345 A1* | 4/2016 | Kostic | A61B 5/1116 5/652 |
| 2017/0098359 A1 | 4/2017 | Sidhu et al. | |
| 2017/0234723 A1 | 8/2017 | Charles et al. | |
| 2018/0303687 A1 | 10/2018 | Moreno et al. | |
| 2018/0374573 A1 | 12/2018 | Bhimavarapu et al. | |
| 2019/0336367 A1 | 11/2019 | Zerhusen et al. | |
| 2020/0197247 A1 | 6/2020 | Nahavandi et al. | |
| 2020/0405192 A1* | 12/2020 | Bhai | A61B 5/747 |

OTHER PUBLICATIONS

Stryker Operations Manual InTouch Critical Care Bed Model FL27, Apr. 2012.
Stryker Operations Manual Epic II Critical Care Bed, Model 2030, Jan. 2010.
Alphacare Umano Ook Snow Hospital Bed Brochure, Nov. 2018.
PCT International Search Report completed date Aug. 27, 2020, for International application No. PCT/US20/39481.
PCT International Written Opinion completed date Aug. 27, 2020, for International application No. PCT/US20/39481.

* cited by examiner

PATIENT SUPPORT APPARATUS WITH IMPROVED USER INTERFACE

BACKGROUND

The present disclosure relates to patient support apparatuses, such as beds, cots, stretchers, operating tables, recliners, or the like.

Conventional patient support apparatuses include user interfaces having a plurality of controls for controlling various features of the patient support apparatus. Such user interfaces often require pressing multiple buttons and/or activating multiple controls in order for the caregiver to carry out the desired functions, thereby making usage of the user interface complex and difficult. User interfaces that are simple to operate and that reduce the work necessary for a caregiver to carry out the function desired by the caregiver are desirable.

SUMMARY

According to various embodiments, an improved patient support apparatus is provided that includes a user interface having one or more navigation controls that simultaneously function as activation controls. That is, the navigation controls not only take the caregiver to a corresponding screen for carrying out a function related to that particular navigation control, but the navigation control also automatically implements that function, thereby saving the caregiver the additional step of manually implementing the function. Further, the automatic implementation of the function is carried out in a smart manner. That is, the automatic implementation of the function is carried out using one or more settings that the caregiver previously used with that particular patient, or it is automatically carried out using one or more settings that were preset by either administrators of the healthcare facility or the manufacturer of the patient support apparatus. Still further, if the caregiver changes one or more of the settings associated with the selected function, not only are the settings changed during that implementation of the function, but the settings are saved and automatically applied to future uses of that function (at least when those future uses are carried out with respect to the same patient). These features reduce the level of work required by the caregiver when utilizing various functions of the patient support apparatus, thereby enabling the caregiver to focus more on patient care, rather than equipment interaction.

According to one embodiment of the present disclosure, a patient support apparatus is provided that includes a support structure, an exit detection system, a user interface, and a controller. The support structure includes a patient support surface adapted to support a patient thereon. The exit detection system is configured to issue an alert when the exit detection system is armed and a patient exits the patient support surface. The user interface includes a display and an exit detection navigation control. The controller, is adapted to, in response to user-activation of the exit detection navigation control, display an exit detection control screen on the display, determine whether a setting of the exit detection system was previously customized for the patient, and arm the exit detection system with the patient-customized setting if the setting was previously customized for the patient or with a preset setting if the setting was not previously customized for the patient.

According to other aspects of the present disclosure, the exit detection navigation control may be physically separated from the display, may be incorporated into the display, and/or may include a first exit detection navigation control displayed on the display and a second exit detection navigation control positioned outside of the display.

In some embodiments, the controller is further configured to, in response to user-activation of the exit detection navigation control, determine if the exit detection system is currently issuing an alert, and to cancel the alert if the exit detection system is determined to be currently issuing an alert.

In some embodiment, the patient-customized setting is a sensitivity level of the exit detection system.

In some embodiments, the exit detection control screen includes a sensitivity control for changing a sensitivity level of the exit detection system, and the controller is further configured to save in a memory a change made by the user to the sensitivity level of the exit detection system using the sensitivity control.

The controller, in some embodiments, is configured to automatically adjust the patient-customized setting according to the change made by the user to the sensitivity level of the exit detection system.

The controller may further be adapted to perform the following in response to a subsequent user-activation of the exit detection navigation control: display the exit detection control screen on the display, and arm the exit detection system with the adjusted patient-customized setting.

In some embodiments, the sensitivity level corresponds to a particular zone. In such embodiments, the exit detection system may comprise a plurality of force sensors adapted to detect a center of gravity of the patient, wherein the exit detection system is configured to issue an exit alert if the patient's center of gravity moves outside of the particular zone.

In some embodiments, a memory is included onboard the patient support apparatus in which the patient-customized setting and the preset setting are stored. In such embodiments, the user interface includes a new patient control and the controller is further configured to erase the patient-customized setting from the memory in response to user-activation of the new patient control, but retain the preset setting in the memory.

The user interface may include a control for allowing the user to modify the preset setting.

According to another embodiment of the present disclosure, a patient support apparatus is provided that includes a support structure, a monitoring system, a user interface, and a controller. The support structure includes a patient support surface adapted to support a patient thereon. The monitoring system is configured, when armed, to monitor a set of conditions of the patient support apparatus and to generate an alert when at least one condition from the set of conditions changes from a desired state to an undesired state. The user interface includes a display and a monitor navigation control. The controller is configured to, in response to user-activation of the monitor navigation control: display a monitoring control screen on the display; determine whether a setting of the monitoring system was previously customized for the patient; and arm the monitoring system with the patient-customized setting if the setting was previously customized for the patient or with a preset setting if the setting was not previously customized for the patient.

According to other aspects of the present disclosure, the controller is further configured to, in response to user-activation of the monitor navigation control, determine if the monitoring system is currently issuing an alert, and to cancel the alert if the monitoring system is determined to be currently issuing an alert.

In some embodiments, the patient-customized setting defines what conditions are in the set of conditions monitored by the monitoring system.

In some embodiments, the monitoring control screen includes a plurality of monitoring controls and each monitoring control corresponds to a particular condition of the patient support apparatus. In such embodiments, the controller is configured to change the set of conditions monitored by the monitoring system based on whether the user activates one or more of the monitoring controls or deactivates one or more of the monitoring controls.

The controller may further be configured to automatically adjust the patient-customized setting in response to the user activating one or more of the monitoring controls or deactivating one or more of the monitoring controls. Still further, the controller may also be adapted to perform the following in response to a subsequent user-activation of the monitor navigation control: display the monitoring control screen on the display, and arm the monitoring system with the adjusted patient-customized setting.

In some embodiments, the set of conditions monitored by the monitoring system includes at least two of the following: a height of the patient support surface, a state of a brake onboard the patient support apparatus, a position of one or more siderails onboard the patient support apparatus, an armed/disarmed state of an exit detection system onboard the patient support apparatus, and an angle of a pivotable back section of the patient support surface.

The patient-customized setting, in some embodiments, also defines a desired state for at least one of the conditions in the set of conditions monitored by the monitoring system. The desired state is a threshold angle for a pivotable back section of the patient support surface in at least one embodiment, and the monitoring system is adapted to issue the alert if the pivotable back section pivots below the threshold angle. Additionally or alternatively, the desired state may be a threshold height for the patient support surface, in which case the monitoring system is adapted to issue the alert if the patient support surface is raised above the threshold height.

In some embodiments, the user interface is adapted to allow the user to customize the threshold angle and/or the threshold height.

In some embodiments, the user interface includes a control for allowing the user to modify the preset setting.

In at least one embodiment, the patient support apparatus further comprises an exit detection system configured to issue an alert when the exit detection system is armed and a patient exits the patient support surface. In such embodiments, the user interface further comprises an exit detection navigation control and the controller is further configured to, in response to user-activation of the exit detection navigation control: display an exit detection control screen on the display; determine whether an exit detection setting of the exit detection system was previously customized for the patient; and arm the exit detection system with the patient-customized exit detection setting if the exit detection setting was previously customized for the patient or with a preset exit detection setting if the exit detection setting was not previously customized for the patient.

In some embodiments, the monitoring system further comprises a plurality of sensors in communication with the controller. The plurality of sensors includes at least two of the following: a side rail sensor adapted to detect a position of a siderail onboard the patient support apparatus, a head-of-bed (HOB) angle sensor adapted to detect an angle of a pivotable back section of the patient support surface, a height sensor adapted to detect a height of the patient support surface, and a bed angle sensor adapted to detect a tilt of the patient support surface.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
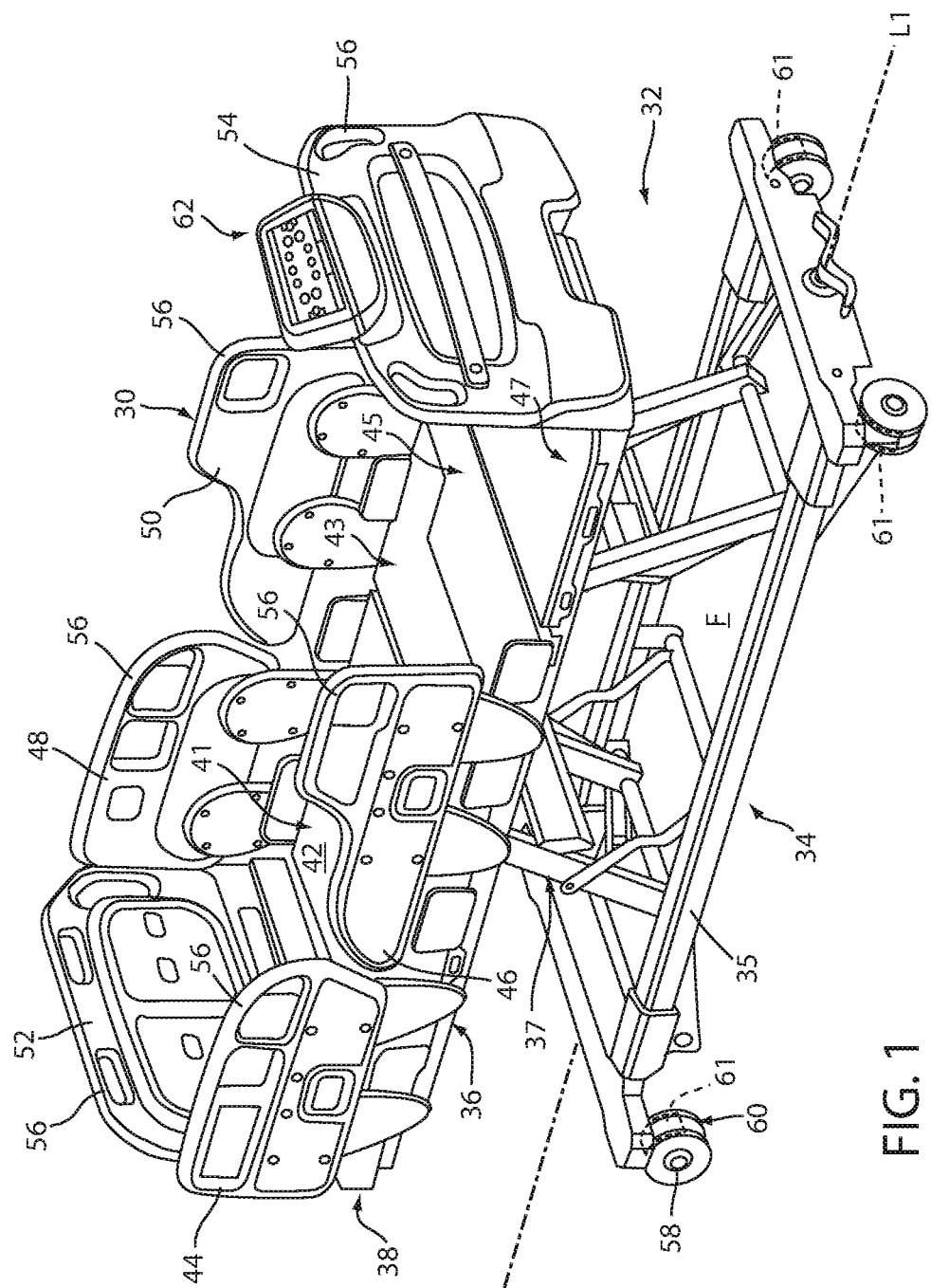
FIG. 1 is a perspective view of a patient support apparatus having a user interface.

An illustrative patient support apparatus 30 that incorporates one or more aspects of the present disclosure is shown in FIG. 1. Although the particular form of patient support apparatus 30 illustrated in FIG. 1 is a bed adapted for use in a hospital or other medical setting, it will be understood that patient support apparatus 30 could, in different embodiments, be a cot, a stretcher, a gurney, a recliner, an operating table, a residential bed, or any other structure capable of supporting a person, whether stationary or mobile and/or whether medical or residential.

A support structure 32 provides support for the patient. The support structure 32 illustrated in FIG. 1 comprises a base 34 and a support frame 36. The base 34 comprises a base frame 35. The support frame 36 is spaced above the base frame 35 in FIG. 1. The support structure 32 also comprises a patient support deck 38 disposed on the support frame 36. The patient support deck 38 comprises several sections, some of which are capable of articulating (e.g., pivoting) relative to the support frame 36, such as a back (Fowler) section 41, a seat section 43, a leg section 45 and a foot section 47. The patient support deck 38 provides a patient support surface 42 upon which the patient is supported. A lift system 37 may be coupled to the support structure 32 to raise and lower the support frame 36, patient support deck 38, and patient support surface 42 to different heights relative to the base frame 35, including to a lowest height relative to the base frame 35. Such a lift system 37 may be like that described in U.S. Patent Application Pub. No. 2017/0246065, filed on Feb. 22, 2017, entitled "Lift Assembly For Patient Support Apparatus," the complete disclosure of which is hereby incorporated herein by reference.

A mattress (not shown) is disposed on the patient support deck 38 during use. The mattress comprises a secondary patient support surface upon which the patient is supported. The base 34, support frame 36, patient support deck 38, and patient support surface 42 each have a head end and a foot end corresponding to designated placement of the patient's head and feet on patient support apparatus 30. The base 34 comprises a longitudinal axis L1 along its length from the head end to the foot end. The construction of the support structure 32 may take on any known or conventional design, and is not limited to that specifically set forth above.

Patient barriers, such as side rails 44, 46, 48, 50 are coupled to the support frame 36 and/or patient support deck 38 and are thereby supported by the base 34. A first side rail 44 is positioned at a right head end. A second side rail 46 is positioned at a right foot end. A third side rail 48 is positioned at a left head end. A fourth side rail 50 is positioned at a left foot end. In the embodiment shown, the head end side rails 44, 48 are mounted to the back section 41 for movement with the back section 41. The foot end side rails 46, 50 are mounted to the support frame 36 for movement with the support frame 36. If patient support apparatus 30 is a stretcher or a cot, there may be fewer side rails. The side rails 44, 46, 48, 50 are movable relative to the back section 41/support frame 36 to a raised position in which the side rails 44, 46, 48, 50 block ingress and egress into and out of patient support apparatus 30, one or more intermediate positions, and a lowered position in which the side rails 44, 46, 48, 50 are not an obstacle to such ingress and egress. In the embodiment shown, the side rails 44, 46, 48, 50 are connected to the back section 41 and/or the support frame 36 by pivotal support arms to form four bar linkages. Such side rails and the manner in which they may be raised/lowered are shown and described in U.S. Patent Application Pub. No. 2017/0172829, filed on Dec. 15, 2016 and entitled "Powered Side Rail For A Patient Support Apparatus," the complete disclosure of which is hereby incorporated herein by reference.

A headboard 52 and a footboard 54 are coupled to the support frame 36. The headboard 52 and footboard 54 may be coupled to any location on patient support apparatus 30, such as the support frame 36 or the base 34. In still other embodiments, patient support apparatus 30 does not include the headboard 52 and/or the footboard 54.

Caregiver interfaces 56, such as handles, are shown integrated into the headboard 52, footboard 54, and side rails 44, 46, 48, 50 to facilitate movement of patient support apparatus 30 over a floor surface F. Additional caregiver interfaces 56 may be integrated into other components of patient support apparatus 30. The caregiver interfaces 56 are graspable by the caregiver to manipulate patient support apparatus 30 for movement, to move the side rails 44, 46, 48, 50, and the like.

Wheels 58 are coupled to the base 34 to facilitate transport over the floor surface F. The wheels 58 are arranged in each of four quadrants of the base 34 adjacent to corners of the base 34. In the embodiment shown, the wheels 58 are caster wheels able to rotate and swivel relative to the support structure 32 during transport. Each of the wheels 58 forms part of a caster assembly 60. Each caster assembly 60 is mounted to the base 34. Brakes 61 may be associated with one or more of the wheels 58 to arrest rotation of the wheels when active. The brakes 61 may be manually or electronically actuated. It should be understood that various configurations of the caster assemblies 60 and/or brakes 61 are contemplated. In addition, in some embodiments, the wheels 58 are not caster wheels and may be non-steerable, steerable, non-powered, powered, or combinations thereof. Additional wheels are also contemplated. For example, patient support apparatus 30 may comprise four non-powered, non-steerable wheels, along with one or more powered wheels. In some cases, patient support apparatus 30 may not include any wheels.

In other embodiments, one or more auxiliary wheels (powered or non-powered), which are movable between stowed positions and deployed positions, may be coupled to the support structure 32. In some cases, when these auxiliary wheels are located between caster assemblies 60 and contact the floor surface F in the deployed position, the auxiliary wheels cause two of the caster assemblies 60 to be lifted off the floor surface F, thereby shortening a wheel base of patient support apparatus 30. A fifth wheel may also be arranged substantially in a center of the base 34.

The mechanical construction of patient support apparatus 30 may be the same as, or nearly the same as, the mechanical construction of the Model 3002 S3 bed manufactured and sold by Stryker Corporation of Kalamazoo, Michigan. This mechanical construction is described in detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 30 can be designed with other types of mechanical constructions, such as, but not limited to, those described in U.S. Pat. No. 7,690,059, issued Apr. 6, 2010, entitled "Hospital Bed," and/or U.S. Pat. No. 8,689,376, issued Apr. 8, 2014, entitled "Patient Handling Device Including Local Status Indication, One-Touch Fowler Angle Adjustment, and Power-On Alarm Configuration", the complete disclosures of both of which are hereby incorporated herein by reference. The mechanical construction of patient support apparatus 30 may also take on forms different from what is disclosed in the aforementioned references.

Additionally, patient support apparatus 30 may include one or more user interfaces 62 supported by the support structure 32 of patient support apparatus 30. The user interfaces 62 may be disposed at the head end, the foot end, and/or on one or more sides of patient support apparatus 30. More specifically, the user interfaces 62 may be attached to the headboard 52, footboard 54, and/or side rails 44, 46, 48, 50, or at any other suitable location, via fasteners, welding, snap-fit connections, or the like. In some versions, each user interface 62 comprises a separate housing fixed to the headboard 52, footboard 54, and/or side rails 44, 46, 48, 50, or other suitable locations. In other versions, the housings of the user interfaces 62 are integrated into the headboard 52, footboard 54, and/or side rails 44, 46, 48, 50. In at least one embodiment, one of the user interfaces 62 is attached to the footboard 54 of patient support apparatus 30 and other user interfaces 62 are attached to one or more of the side rails 44, 46, 48, 50. The user interface 62 attached to the footboard 54 shall be described in detail, but the features and functions to be described are equally applicable to the other user interfaces 62 that may be located elsewhere on patient support apparatus 30.

Figure 2:
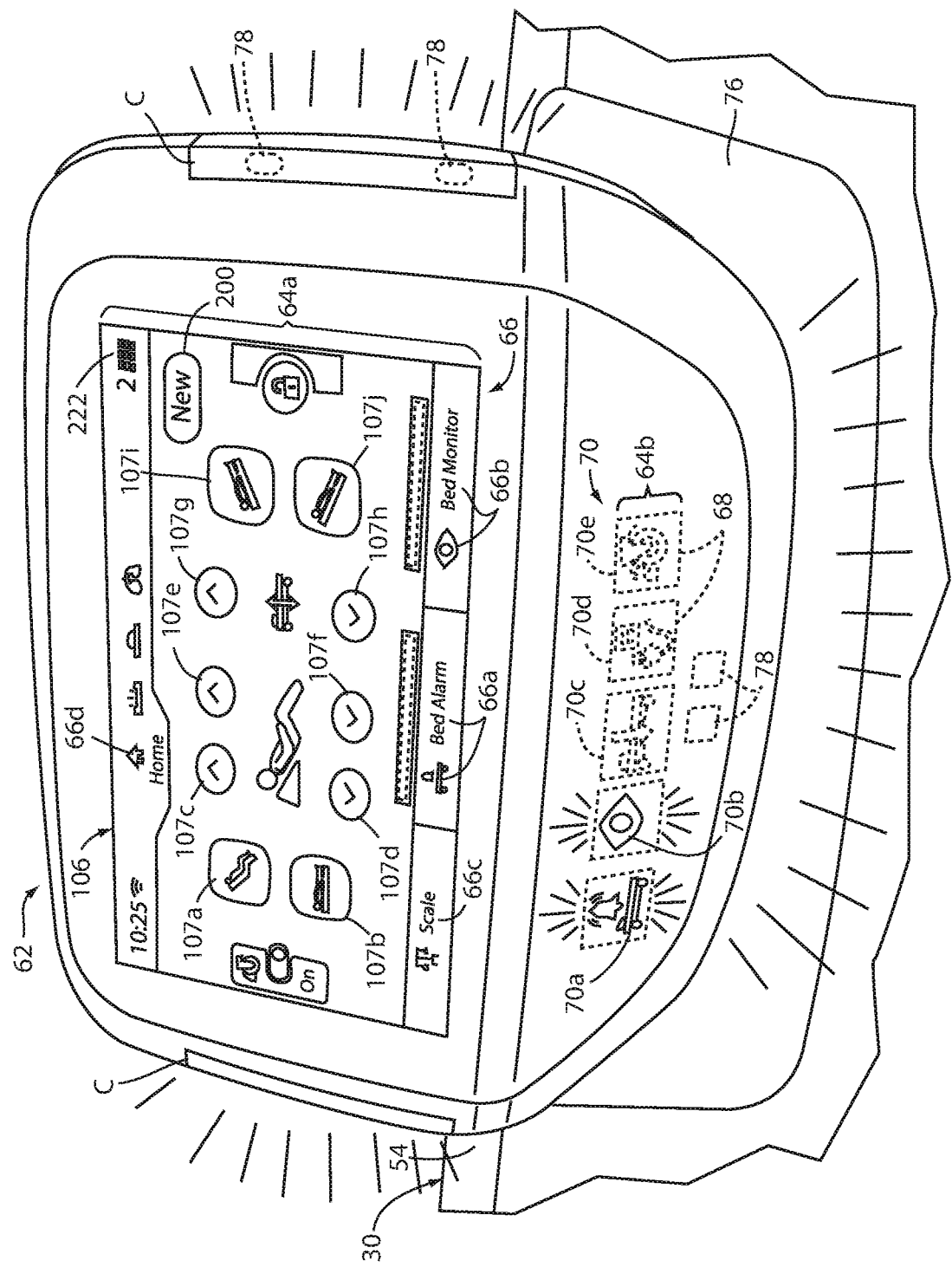
FIG. 2 is a partial perspective view of the user interface depicted in FIG. 1.

FIG. 2 depicts a perspective view of user interface 62 attached to the footboard 54. User interface 62 includes a display 64a. Display 64a may be a touchscreen-type display, although it will be understood that a non-touchscreen display may alternatively be used. Display 64a displays one or more visual indicators, one or more controls, and/or one or more control screens, as will be discussed more below. Display 64a may comprise an LED display, OLED display, or another type of display.

Display 64a is configured to display a plurality of different screens thereon, only one of which is shown in FIG. 2. Specifically, display 64a is shown in FIG. 2 displaying a motion control screen 106. Motion control screen 106 includes a plurality of motion controls 107a-i that, when touched, cause movement of the associated component(s) of patient support apparatus 30. Thus, for example, pressing and holding motion control 107c causes back section 41 to be pivoted upwardly, while pressing and holding motion control 107d causes back section 41 to be pivoted downwardly. If the user wishes to control other aspects of patient support apparatus 30 besides movement, he or she can navigate to different screens that include different controls and/or other information about patient support apparatus. Thus, for example, if the user presses navigation control 66a, user interface 62 displays an exit detection control screen 108 (FIG. 4) that allows the user to control various aspects of exit detection system 102. If the user presses navigation control 66b, user interface 62 displays a bed monitor control screen 110 (FIG. 6) that allows the user to control various aspects of the bed monitor system 104. If the user presses navigation control 66c, user interface 62 displays a scale screen (not shown) that allows the user to take a patient weight reading and/or control other aspects of the scale system. Still further, if the user presses home navigation control 66d, user interface 62 displays a home screen that, in some embodiments, includes controls for accessing all of the functionality of patient support apparatus 30.

In some embodiments, navigation controls 66a-d are displayed on all, or substantially all, of the screens that are displayable on display 64a. By including navigation controls 66a-d on all, or substantially all, of the screens shown on display 64a, the user is always able to easily navigate to a different screen by simply pressing the desired navigation control 66a-d on display 64a. This avoids the needs for scrolling back, or otherwise sorting through multiple levels of screens, to get to the desired screen. In some embodiments, user interface 62 may be configured to not display a navigation control 66 if display 64 is currently displaying a screen that corresponds to a particular navigation control 66. Thus, for example, if a user selects scale navigation control 66c and user interface 62 displays a scale screen (not shown) on display 64a, user interface 62 is configured to still display navigation controls 66a, 66b, and 66d on the scale screen but may, in some embodiments, omit navigation control 66c on the scale screen. Alternatively, or additionally, any of navigation controls 66a-d may be physical controls that are separated from display 64a and always available to the user.

User interface 62, in some embodiments, also includes a dashboard 64b that communicates the current states of various conditions of patient support apparatus 30 to a caregiver. Dashboard 64b comprises a plurality of indicia 70 that are illuminated via first light emitters 68 to thereby act as visual indicators for indicating the current state of different conditions of patient support apparatus 30. For example, a first indicium 70a (e.g., a graphical symbol of an alarm over a bed) is illuminated when exit detection system 102 is armed, a second indicium 70b (e.g., a graphical symbol of an eye) is illuminated when bed monitor system 104 is armed, a third indicium 70c (e.g., a graphical symbol of an arrow and bed) is illuminated when the bed is at its lowest height (or below a threshold height), a fourth indicium 70d (e.g., a graphical symbol of an unplugged AC power cord) is illuminated when the patient support apparatus 30 is plugged into an electrical wall outlet and a fifth indicium 70e (e.g., a graphical symbol of a lock and wheel) is illuminated when the brakes are activated. Any one or more of these indicia 70a-e may be illuminated a different color when the associated condition is in another state (e.g. the brake is deactivated, exit detection system 102 is disarmed, etc.) and/or one or more of them may alternatively not be illuminated at all when the associated condition is in another state. Fewer or additional indicia 70 may be included as part of dashboard 64b.

Dashboard 64b, unlike display 64a, retains the illumination of one or more of indicia 70a-e at all times. That is, display 64a is configured in some embodiments to go blank after a predetermined time period elapses without usage. Dashboard 64b, however, retains the illumination of the various indicia 70 even after display 64a goes blank, thereby providing the caregiver with information about the status of patient support apparatus 30 when display 64a is blank. Thus, for example, if the brake is not activated and indicium 70e is illuminated with an amber or red color, this illumination remains for as long as the brake remains inactive, even if display 64a times out and goes to sleep (or otherwise goes blank).

Still referring to FIG. 2, one or more reflective surfaces 76 may be located on patient support apparatus 30 proximate user interface 62. The reflective surfaces 76 may be disposed relative to user interface 62 such that one or more second light emitters 78 supported by the housing of user interface 62 project light away from user interface 62 toward the reflective surfaces 76 to be reflected off the reflective surfaces 76 and outward from patient support apparatus 30 to act as another visual indicator.

The first light emitters 68 and/or the second light emitters 78 may comprise RGB LEDs ("Red-Green-Blue Light Emitting Diodes"). The first light emitters 68 and/or the second light emitters 78 may comprise a single RGB LED, or may comprise a plurality of LEDs. The first and second light emitters 68, 78 may also comprise one or more incandescent bulbs, halogen lamps, neon lamps, fluorescent tubes, and/or any other types of light emitting devices. Some of the light emitters 78 may be located on the sides of user interface 62 to illuminate through light-transmitting covers C attached to the housing of user interface 62.

Figure 3:
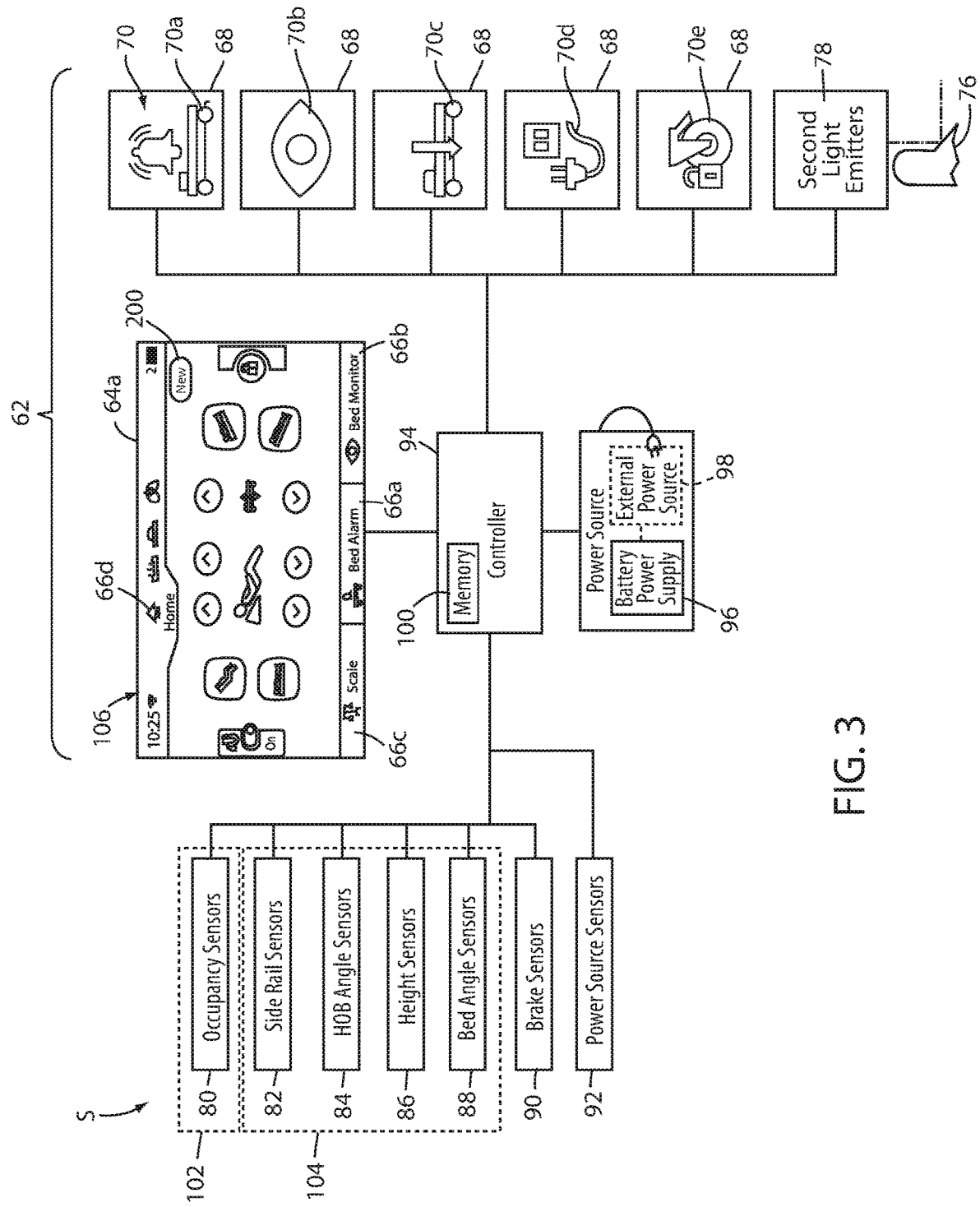
FIG. 3 is a schematic diagram of the components of the user interface of FIG. 1 shown coupled to a plurality of sensors.

FIG. 3 illustrates user interface 62 coupled to a sensor system S. Sensor system S includes a plurality of sensors that detect various conditions of patient support apparatus 30, including, but not necessarily limited to, the conditions that are indicated by indicia 70*a-e*. As shown in FIG. 3, user interface 62 includes a controller 94 having one or more microprocessors, microcontrollers, field programmable gate arrays, systems on a chip, discrete circuitry, and/or other suitable hardware, software, or firmware that is capable of carrying out the functions described herein. Controller 94 is coupled to display 64*a*, dashboard 64*b*, and light emitters 68, 78 in a manner that allows controller 94 to control display 64*a* and light emitters 68, 78 (connections shown schematically in FIG. 3). Controller 94 may communicate with display 64*a* and light emitters 68, 78 via wired or wireless connections to perform the functions described herein. Power to display 64*a*, light emitters 68, 78 and/or controller 94 may be provided by a battery 96 and/or an external power source 98.

Controller 94 is configured to process instructions and algorithms stored in memory 100 to control operation of display 64*a* and dashboard 64*b* and, in some embodiments, to control operation of various other components of the patient support apparatus 30. The instructions followed by controller 94 in carrying out the functions described herein, as well as the data necessary for carrying out these functions, are stored in memory 100.

Sensor system S comprises sensors 80, 82, 84, 86, 88, 90, and 92 and is integrated into patient support apparatus 30 to generate one or more output signals corresponding to various states of patient support apparatus 30. Controller 94 generates command to control display 64*a*, dashboard 64*b*, and the light emitters 68, 78 based on the signals that controller 94 receives from the sensors 80, 82, 84, 86, 88, 90, 92 of sensor system S.

Sensor system S includes one or more force sensors 80, side rail sensors 82, HOB angle sensors 84, height sensors 86, tilt sensors 88, brake sensors 90, and power source sensors 92. Force sensors 80 output signals in response to downward forces exerted onto support deck 38 by the patient and/or objects, and force sensors 80 may be implemented as load cells, although other types of force sensors may be used. Side rail sensors 82 output signals that indicate a current position of side rails 44, 46, 48, 50 so that controller 94 can determine whether the side rails 44, 46, 48, 50 are in the raised position (up), lowered position (down), or in one of the intermediate positions. HOB angle sensor 84 outputs signals that indicate a current angle of the back section 41 so that controller 94 can determine whether the back section 41 is at or above a preset angle relative to the support frame 36 or at less than the preset angle. Height sensors 86 output signals that indicate a current height of the support frame 36/patient support deck 38 so that controller 94 can determine whether patient support apparatus 30 is at the lowest height or not. Tilt angle sensors 88 output signals that indicate a current tilt angle of the patient support surface 42 so that controller 94 can determine whether the patient support surface 42 is flat or not flat. Brake sensors 90 output signals that indicate whether the brakes are active (on) or inactive (off). Power source sensors 92 output signals that indicate whether or not the AC power plug that provides power from the external power source 98 to patient support apparatus 30 is plugged into a corresponding outlet (e.g., wall outlet) to receive external power. These sensors 80, 82, 84, 86, 88, 90, 92 may include one or more load cells, pressure sensors such as piezoelectric and piezoresistive sensors, Hall Effect sensors, capacitive sensors, resonant sensors, thermal sensors, limit switches, gyroscopes, accelerometers, motion sensors, ultrasonic sensors, range sensors, potentiometers, magnetostrictive sensors, electrical current sensors, voltage detectors, and/or any other suitable types of sensors for carrying out their associated functions. When the sensor system S outputs signals indicative of a state change, controller 94 may cause activation/illumination of a respective state indicator 65, indicium 70*a*, 70*b*, 70*c*, 70*d*, 70*e*, and/or reflective surface 76 in the manner described herein.

Force sensors 80 are part of an exit detection system 102 that determines if the occupant has exited patient support apparatus 30. Force sensors 80 can also be part of a scale system that detects the weight of an occupant of patient support apparatus 30, the details of which are not described herein. Force sensors 80 are adapted to detect downward forces exerted on the patient support surface 42, i.e. by an occupant of support deck 38. Thus, when an occupant is positioned on support deck 38 and substantially still (i.e. not moving in a manner involving accelerations that cause forces to be exerted against support deck 38), force sensors 80 will detect the weight of the occupant. Force sensors 80 can also be used to determine a center of gravity of the occupant in order to determine if the occupant is about to exit patient support apparatus 30. In alternative embodiments, the outputs from force sensors 80 are analyzed, not to determine a center of gravity, but instead to determine a weight distribution and/or a change in weight distribution, such as by determining one or more ratios of the relative weights sensed by force sensors 80 and using them to determine if the occupant is about to exit patient support apparatus 30. In still other embodiments, force sensors 80 may be modified to detect forces other than, or in addition to, the downward forces exerted by the occupant. Other types of sensors may additionally or alternatively be used for determining if the patient has exited, or is about to exit.

The particular structural details of exit detection system 102 can vary widely. In some embodiments, exit detection system 102 is constructed in accordance with the exit detection system described in U.S. Pat. No. 5,276,432, issued Jan. 4, 1994, entitled "Patient Exit Detection Mechanism for Hospital Bed," the complete disclosure of which is hereby incorporated herein by reference. In such embodiments, exit detection system 102 may include multiple zones that trigger an alert when the patient's center of gravity travels outside of the zone. In this manner, exit detection system is able to have its sensitivity selected by the caregiver, as will be discussed in more detail below. Other types of exit detection systems may also or alternatively be used.

Exit detection system 102 is configured to be armed and disarmed. When armed, exit detection system 102 issues an alert when the occupant exits patient support surface 42, or is about to exit patient support apparatus 30. The alert issued by exit detection system 102 includes activation/illumination and/or changing a color, frequency, or illumination pattern of light emitted/projected from one or more of the lights of user interface 62. Such lights include, but are not limited to, the lights that shine on reflective surface 76.

User interface 62 communicates with controller 94 and allows the caregiver to control various aspects of exit detection system 102, such as, but not limited to, arming or disarming exit detection system 102, customizing a setting of exit detection system 102, such as customizing a sensitivity level of exit detection system 102, and cancelling an alert issued by exit detection system 102. Other customizable settings for exit detection system 102 are possible.

The sensitivity level of exit detection system 102 can be set to low, medium, or high. The sensitivity level settings can correspond to different zones of patient support apparatus 30 which are monitored by exit detection system. For example, with the low sensitivity level setting selected, exit detection system monitors a first, relatively large zone that is generally positioned near the center of the patient support surface 42. With the medium sensitivity level setting selected, exit detection system monitors a second zone at or near the center of the patient support surface 42 which is smaller than the first zone. With the high sensitivity level setting selected, exit detection system monitors a third zone at or near the center of the patient support surface 42 which is smaller than both the first and second zone.

One or more of the side rail sensors 82, HOB angle sensors 84, height sensors 86, and bed angle sensors 88 are part of a bed monitor system 104 (FIG. 3) that determines if any monitored conditions of patient support apparatus 30 are in an undesired state. Other monitored conditions may be included within bed monitor system 104, such as, but not limited to, the state of the brake, the state of the power source (e.g. battery versus outlet power), and the state of exit detection system 102 (armed or disarmed). Such other monitored conditions may utilize additional sensors for determining the state of these other conditions of patient support apparatus 30. The particular structural details of bed monitor system 104 can vary widely. An exemplary bed monitor system is described in U.S. Pat. No. 8,844,076, filed on Jan. 27, 2014, entitled "Patient Handling Device Including Local Status Indication, One-Touch Fowler Angle Adjustment, and Power-On Alarm Configuration," the complete disclosure of which is hereby incorporated herein by reference. Other types of bed monitor systems may be used.

Bed monitor system 104 is configured to be armed and disarmed. When armed, bed monitor system 104 issues an alert when at least one monitored condition of patient support apparatus 30 is in an undesired state, which may include when one or more of the side rails are down, when the HOB angle is less than the preset angle, when the bed is not flat, or when the bed height is above a threshold height. The alert issued by bed monitor system 104 can include activation/illumination of one or more lights, and/or changing the color, frequency, or illumination pattern of one or more lights, such as, but not limited to, the lights that emit light onto reflective surface 76.

User interface 62 communicates with controller 94 and enables the caregiver to control one or more aspects of bed monitor system 104, such as, but not limited to, arming or disarming bed monitor system 104, customizing a setting of bed monitor system 104, such as customizing which conditions of bed monitor system 104 are monitored and, in some cases, customizing the desired and undesired states for the monitorable conditions, and cancelling an alert issued by bed monitor system 104. Other customizable settings for bed monitor system 104 are possible. Display 64*a* displays information regarding bed monitor system 104, such as, but not limited to, displaying a bed monitor control screen, displaying an alert issued by bed monitor system 104, and displaying a setting of the bed monitor system 104, such as displaying the conditions of bed monitor system 104 currently being monitored or displaying a customized desired state of the monitored condition.

For example, the position of one or more of the side rails 44, 46, 48, 50, the HOB angle, the bed angle, and the bed height are monitorable conditions of bed monitor system 104. The monitoring setting for each of these conditions can be set to on, e.g. being monitored, or off, e.g. not being monitored. Of these monitored conditions, at least the preset angle for the HOB angle can be set, for example to 30 degrees or 45 degrees.

FIGS. 2 and 3 illustrates one example of a motion control screen 106 that can be displayed on display 64*a*. Motion control screen 106 includes a plurality of controls, which can include touchscreen controls, non-touchscreen controls, or a combination thereof. The controls may perform a variety of different functions, and the number, function, lay-out, size, and/or other characteristics of these controls may vary from what is shown in FIGS. 2 and 3, and may also vary depending upon what screen is being displayed at a given time by display 64*a*.

In the particular example of FIGS. 2 and 3, the controls include exit detection navigation control 66*a* and bed monitor navigation control 66*b*. Each of these controls allow the user to navigate to an associated control screen. For example, when exit detection navigation control 66*a* is pressed, controller 94 displays an exit detection control screen (e.g. screen 108 of FIG. 4) on display 64*a*. The exit detection control screen 108 is used by a caregiver or other user to control aspects of exit detection system 102, as described in further detail below. Briefly, the exit detection control screen 108 enables the caregiver to arm and/disarm the exit detection function of exit detection system 102, as well as to change one or more of the customizable settings associated with the exit detection function.

When the bed monitor navigation control 66*b* is pressed, controller 94 displays a bed monitor control screen (e.g. screen 110 of FIG. 6) on display 64*a*. The bed monitor control screen 110 is used by a caregiver or other user to control aspects of bed monitor system 104, as described in further detail below. Briefly, the bed monitor control screen 110 enables the user to arm and/disarm the bed monitor function of bed monitor system 104, as well as to change one or more of the customizable settings associated with the bed monitor function.

Motion control screen 106 may be displayed initially after patient support apparatus 30 is powered on, or it may be displayed in response to a caregiver navigating to it from another screen. It will be understood that the particular layout shown in FIGS. 2 and 3 is only one of a large variety of different ways in which controller 94 may present a motion control screen 106. It will also be understood that exit detection navigation control 66*a* and the bed monitor navigation control 66*b* are provided on other screens or elsewhere on user interface 62.

Figure 4:
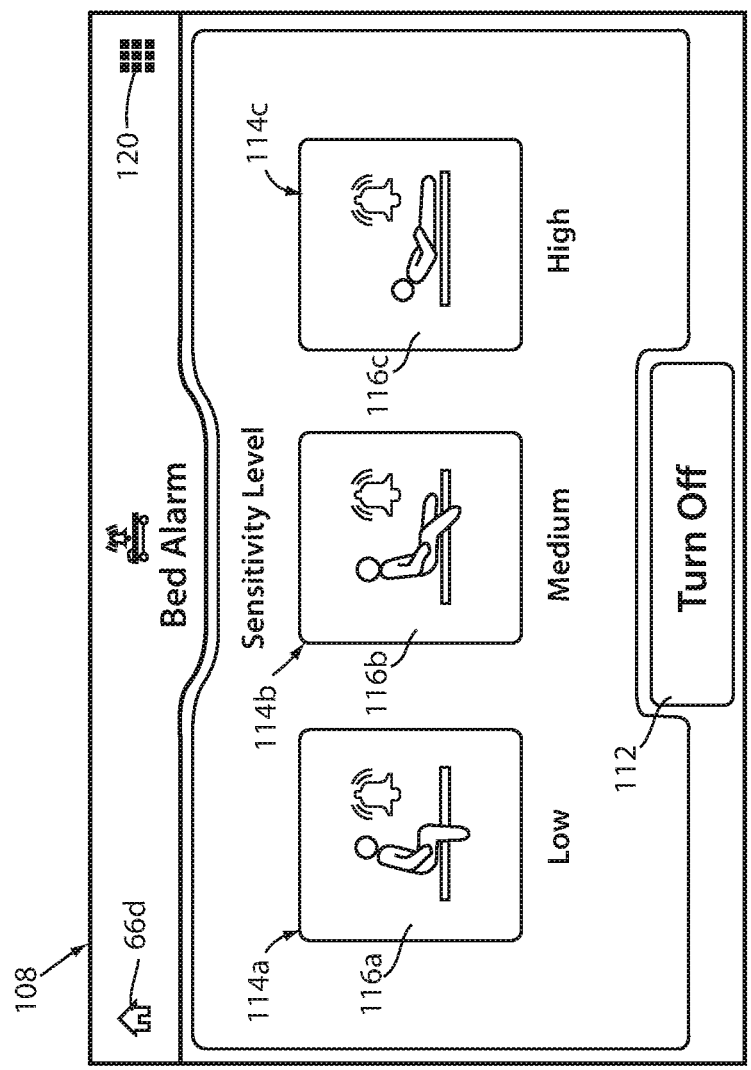
FIG. 4 is an illustrative exit detection control screen that may be displayed on a display of the user interface of FIG. 2.

Referring to FIG. 4, exit detection control screen 108 includes an arm/disarm control 112 for disarming exit detection system 102. Upon user-activation of the arm/disarm control 112, controller 94 is operable to disarm exit detection system 102. Subsequent selection of the arm/disarm control 112 rearms exit detection system 102.

Exit detection control screen 108 also includes setting controls 114*a*, 114*b*, 114*c* and associated setting indicators 116*a*, 116*b*, 116*c*. Each setting control 114*a*, 114*b*, 114*c* corresponds to one of the sensitivity levels of exit detection system 102. Selection of control 114*a* sets exit detection system 102 to a low sensitivity level (e.g. much patient movement is required before an exit alert is triggered); selection of control 114*b* sets exit detection system 102 to a medium sensitivity level; and selection of control 114*c* sets exit detection system 114 to a high sensitivity level (e.g. very little movement is required to trigger an exit alert).

The setting indicators 116a, 116b, 116c indicate to the caregiver whether the associated sensitivity level is currently being utilized by exit detection system 102. The setting indicators 116a, 116b, 116c are displayed on the screen 108 in a first color when the associated sensitivity level setting is unselected and in a second color when the associated sensitivity level setting is selected. In the illustrated example of screen 108, the low and high sensitivity level settings are unselected, and their associated setting indicators 116a, 116c are generated on the screen 108 in gray, and the medium sensitivity level setting is selected, and its associated setting indicator 116b is displayed on the screen 108 in green. The setting indicators 116a, 116b, 116c may alternatively employ text or graphics, or other forms of visual content, to indicate the current sensitivity level.

Exit detection control screen 108 also includes a home navigation control 66d and a menu navigation control 122 for navigating away from the exit detection control screen 108. Upon user-activation of the home navigation control 66d, controller 94 is operable to display a home screen (not shown) on display 64a. Upon user-activation of the menu navigation control 122, controller 94 is operable to display a menu screen (not shown) on display 64a.

When exit detection navigation control 66a on user interface 62 is selected, not only does controller 94 react by automatically displaying exit detection control screen 108 on display 64a, it also automatically arms exit detection system 102. Thus, exit detection navigation control 66a performs dual functions in response to a single action by the caregiver—it brings the user to exit detection control screen 108 and it activates exit detection system 102. This saves the user the extra step, prevalent in many prior art patient support apparatuses, of having to press a first button (or other control) in order to get to an exit detection control screen and then, once at that screen, press a second button (or other control) to activate the exit detection system 102. By performing two functions (navigation and auto-arming) in response to a single touch by the caregiver of a single control, controller 94 streamlines the usage of exit detection system 102.

Additionally, controller 94 is configured to not only automatically arm exit detection system 102 in response to the user touching navigation control 66a, but it is also configured to automatically arm exit detection system 102 using either a preset setting or a patient-customized setting that was previously selected by the caregiver for the particular patient who is now assigned to patient support apparatus 30. These features are discussed in more detail below with respect to exit detection management algorithm 124 (FIG. 5).

Figure 5:
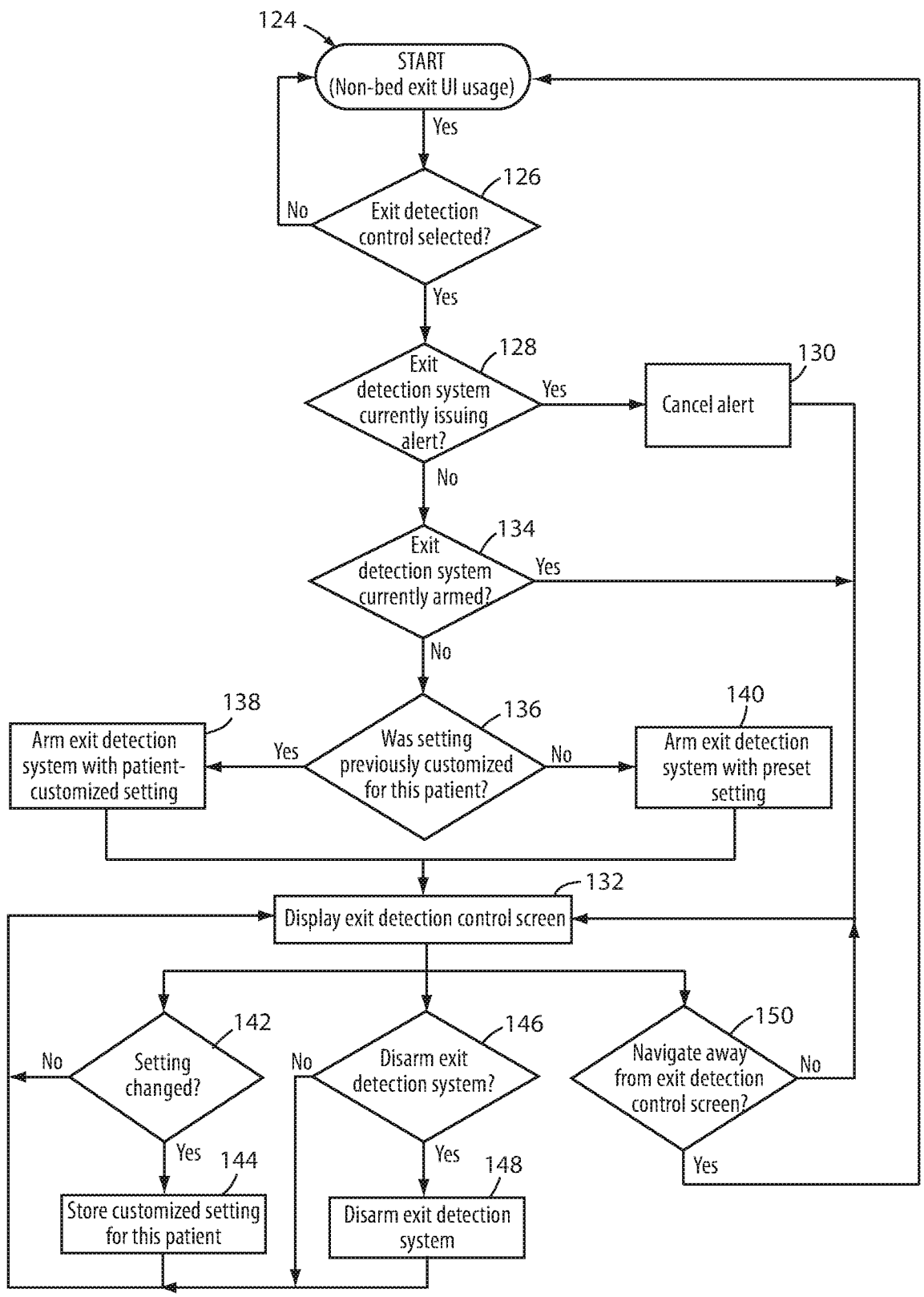
FIG. 5 is an exit detection management algorithm executed by a controller of the user interface.

When a user touches exit detection navigation control 66a on user interface 62, controller 94 begins following exit detection management algorithm 124, one example of which is shown in FIG. 5. Exit detection management algorithm 124 begins at step 126 when exit detection navigation control 66a is selected by the caregiver. Prior to this, the caregiver can be using user interface 62 to perform other functions and display 64a may be displaying a screen other than exit detection control screen 108, such as motion control screen 106 of FIG. 2.

After exit detection navigation control 66a is selected, controller 94 proceeds to step 128 where it determines if exit detection system 102 is currently issuing an alert. Such an alert is issued if exit detection system 102 is armed and the occupant exits the patient support surface 42. If exit detection system 102 is currently issuing an alert, controller 94 proceeds to step 130 and cancels the alert, such as by deactivating first light emitter 68 and/or second light emitter 78 and/or other lights. In another example, controller 94 can cancel the alert by changing the color, frequency, or illumination pattern of light projected from the first light emitter 68 and/or second light emitter 78, and/or still other lights. In another example, an issued alert can comprise emitting an audible alarm from a speaker on user interface 62, elsewhere on patient support apparatus 30, or remote from patient support apparatus 30, and controller 94 can cancel the alert by silencing the audible alarm. After cancelling the alert, controller 94 proceeds to step 132 and displays exit detection control screen 108 on display 64a.

If exit detection system 102 is not currently issuing an alert, from step 128 controller 94 proceeds to step 134, where it determines if exit detection system 102 is currently armed. If exit detection system 102 is currently armed, controller 94 proceeds to step 132 and displays exit detection control screen 108 on display 64a.

If exit detection system 102 is not currently armed, controller 94 proceeds to step 136 and determines whether a setting was previously customized for the patient currently assigned to patient support apparatus 30. If a setting was previously customized for the patient currently assigned to patient support apparatus 30, controller 94 proceeds from step 136 to step 138 and arms exit detection system 102 with the patient-customized setting. If no settings were previously customized for the patient currently assigned to patient support apparatus 30, controller 94 proceeds from step 136 to step 140 where it arms exit detection system 102 with a preset setting. From both steps 138 and step 140, controller 94 proceeds to step 132 where it displays the exit detection control screen 108 and allows the caregiver to utilize the controls and functionality of control screen 108.

Before turning to the operation of control screen 108, it should be noted that the customized setting used in step 138 and the preset setting used in step 140 both refer to, in at least one embodiment, the sensitivity level of exit detection system 102. It will be understood, however, that the settings referred to in steps 138 and 140 may refer to and/or include other settings associated with exit detection system 102. For example, the setting referred to in steps 138 and 140 may relate to one or more characteristics of the alert that is issued when exit detection system 102 is triggered, such as which lights, if any, are activated, what sounds, if any, are activated (and/or their volume level), and/or if the alert is to be communicated to a remote location and, if so, how such communication takes place and/or to what devices the communication is to be forwarded. Still other types of settings may be incorporated into steps 138 and 140.

It will also be understood that, in some embodiments, the setting referred to in steps 138 and 140 may refer to multiple settings such that controller 94 either automatically arms exit detection system 102 using multiple patient-customized settings at step 138 or it arms exit detection system 102 using multiple preset settings. Still further, in some embodiments, controller 94 may automatically arm exit detection system 102 using a combination of patient-customized settings and preset settings, choosing the patient-customized settings over the preset settings whenever such patient-customized settings have been previously defined for the current patient, and using the preset settings whenever no patient-customized settings have been previously defined.

When exit detection control screen 108 is displayed at step 132 (FIG. 5), the caregiver is able to disarm exit detection system 102 (which was just automatically armed at step 138 or 140) via arm/disarm control 112, as well as to change one or more of settings via controls 114a, 114b, 114c. While exit detection control screen 108 is being displayed, controller 94 monitors user interface 62 to see if the caregiver activates one or more functions associated with screen 108, and follows steps 142 through 150 of algorithm 124.

If the caregiver makes any changes to the settings of exit detection system 102 while exit detection control screen 108 is displayed (e.g. selects a different sensitivity level by touching one of controls 114a, 114b, or 114c), controller 94 not only implements those changes immediately for exit detection system 102, but it also saves those changes in memory and uses them as patient-customized settings whenever exit detection system 102 is armed in the future (at least for that same patient). In other words, setting controls 114a, 114b, and 114c not only function as controls for changing the current settings of exit detection system 102, but they also automatically customize those settings for the particular patient who is currently assigned to patient support apparatus 30.

For example, if a patient A is currently occupying patient support apparatus 30 and the caregiver arms exit detection system 102 by touching navigation control 66a, controller 94 automatically arms exit detection system 102 and displays exit detection control screen 108. If this is the first time that exit detection system 102 has been armed for patient A, controller 94 follows step 140 and arms exit detection system 102 using the preset setting which, in at least one embodiment, refers to the medium sensitivity level. After arming exit detection system 102 at this medium sensitivity level at step 140, controller 94 displays exit detection control screen 108 and allows the user to change the sensitivity level of exit detection system 102 via controls 114a, 114b, and 114c. If the user selects, say, control 114a, controller 94 changes the sensitivity level of exit detection system 102 to "low." Further, controller 94 also stores this "low" setting in memory and automatically uses it for all the future times it arms exit detection system 102 for patient A. Thus, if exit detection system 102 is later disarmed (say, while patient A exits from patient support apparatus 30 and subsequently returns), and exit detection system 102 is re-armed with patient A onboard, controller 94 will follow step 138 of algorithm and automatically re-arm the exit detection system using the "low" sensitivity level. In this manner, once a caregiver selects a sensitivity level for a particular patient, every time the caregiver re-arms exit detection system 102 with that particular patient onboard, controller 94 automatically selects the sensitivity level that the caregiver previously selected.

Sensitivity controls 114a-c therefore not only change the current sensitivity level of exit detection system 102, but they also define the patient-customized sensitivity level for future usage of exit detection system 102 with that particular patient. Still further, if a caregiver has already customized a sensitivity level for exit detection system 102 for a particular patient, he or she can use sensitivity controls 114a-c to change the previous customization for that particular patient. This is done by merely selecting a different sensitivity control 114a-c on screen 108.

This process of customizing the sensitivity level of exit detection system 102 for a particular patient is illustrated in steps 142 and 144 of algorithm 124 (FIG. 5). If the caregiver selects a different one of controls 114a-c than the one selected automatically by controller 94 at step 138 or step 140, controller 94 implements this change at step 142. After step 142, it proceeds to step 144 where it records the change in memory 100 and sets (or resets) the patient-customized setting to match the recorded change. As a result, the next time controller 94 executes step 136, it will proceed to step 138 and implement the patient-customized setting that was stored previously at step 144.

If the caregiver presses the arm/disarm control 112 on the exit detection control screen 108 at step 146 (FIG. 5), controller 94 moves to step 148 where it disarms exit detection system 102. After disarmament of exit detection system 102, controller 94 continues to display the exit detection control screen 108 on display 64a. In some embodiments, controller 94 changes the label on arm/disarm control 112 from "turn off" to "turn on" after the caregiver has disarmed exit detection system 102 and toggles these two labels back and forth as the caregiver switches between arming and disarming exit detection system 102. Alternatively, after disarmament of exit detection system 102, controller 94 may be configured to display a different screen on display 64a, such as motion control screen 106 of FIGS. 2 and 3, or another screen (not shown). In one example, controller 94 displays a confirmation screen on display 64a which confirms that exit detection system 102 has been disarmed, after which controller 94 displays the exit detection control screen 108, motion control screen 106, or another screen (not shown) on display 64a.

If the caregiver navigates away from the exit detection control screen 108, such as by selecting the home navigation control 66d or the menu navigation control 122 on the exit detection control screen 108 at step 150, controller 94 returns to the start of the algorithm 124 the next time exit detection navigation control 66a is touched.

It will be understood that, in some embodiments, the preset setting used at step 140 is permanently set by the manufacturer of patient support apparatus 30 and cannot be changed. It will also be understood that, in some alternative embodiments, patient support apparatus 30 can be constructed in a manner that allows healthcare administrators, or other authorized personnel, to change the preset setting used at step 140. In these latter embodiments, healthcare administrators can override the factory-defined preset setting and choose a different preset setting that better suits their particular needs. However, even if the healthcare facility decides to change the preset setting to one that better suits their needs, the caregiver can still customize this setting to a particular patient in the manner just described.

It will also be understood that various changes may be made to exit detection management algorithm 124 from the particular implementation shown in FIG. 5, such as changing the order of one or more steps, adding one or more additional steps, omitting one or more of the existing steps, and/or modifying one or more of the existing steps. In one such example, the particular order of step 132 is changed such that it occurs earlier than shown, such as between step 126 and step 128. Still other locations of step 132 within algorithm 124 may also be implemented.

Figure 6:
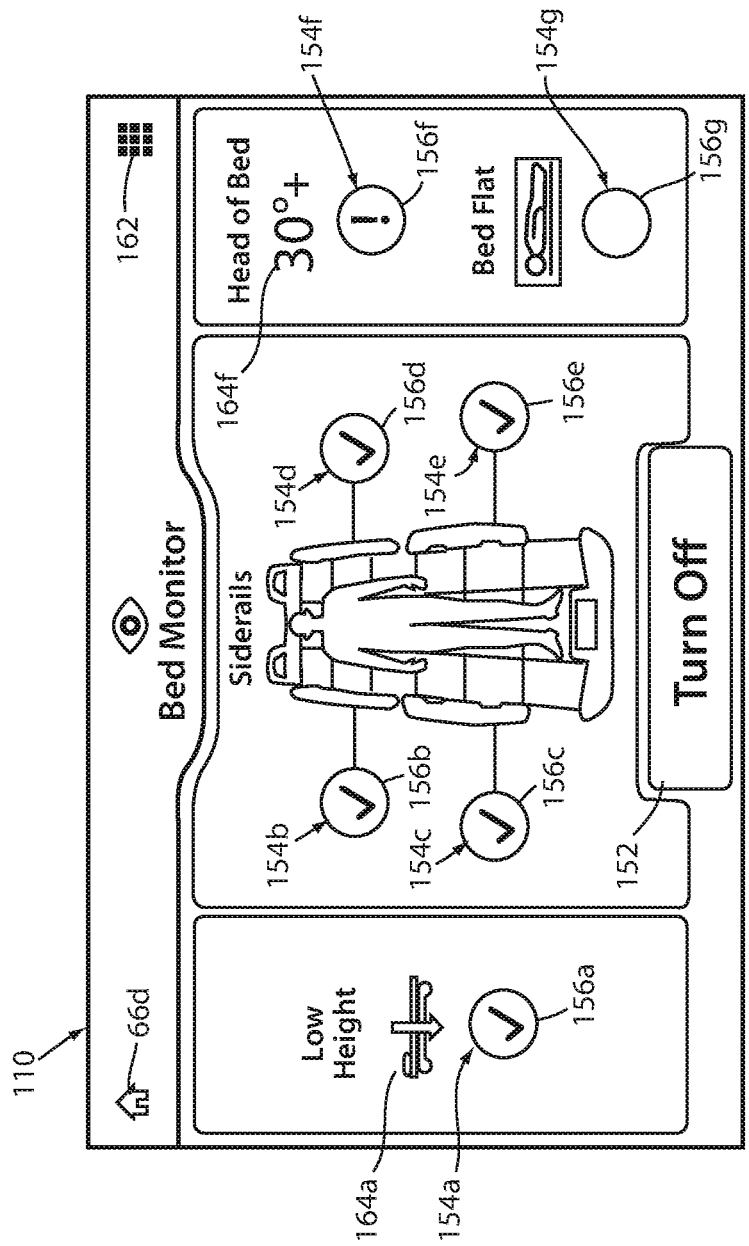
FIG. 6 is an illustrative bed monitor control screen that may be displayed on the display.

Returning to FIG. 2, when the user touches bed monitor navigation control 66b, controller 94 displays bed monitor control screen 110, shown in FIG. 6, on display 64a. The touching of bed monitor navigation control 66b also causes controller 94 to automatically arm the bed monitoring system 104. Bed monitor navigation control 66b therefore performs a dual function in response to a single action by the caregiver—it brings the user to bed monitor control screen 110 and it activates bed monitoring system 104. As with the dual function of exit detection navigation control 66a, the dual function of bed monitor navigation control 66b saves the user the extra step, prevalent in many prior art patient support apparatuses, of having to press a first button (or other control) in order to get to a bed monitoring control screen and then, once at that screen, press one or more additional buttons (or other controls) to activate the bed monitoring system 104. By performing two functions (navigation and auto-arming) in response to a single touch by the caregiver of a single control, controller 94 streamlines the usage of the bed monitoring system 104.

Figure 8:
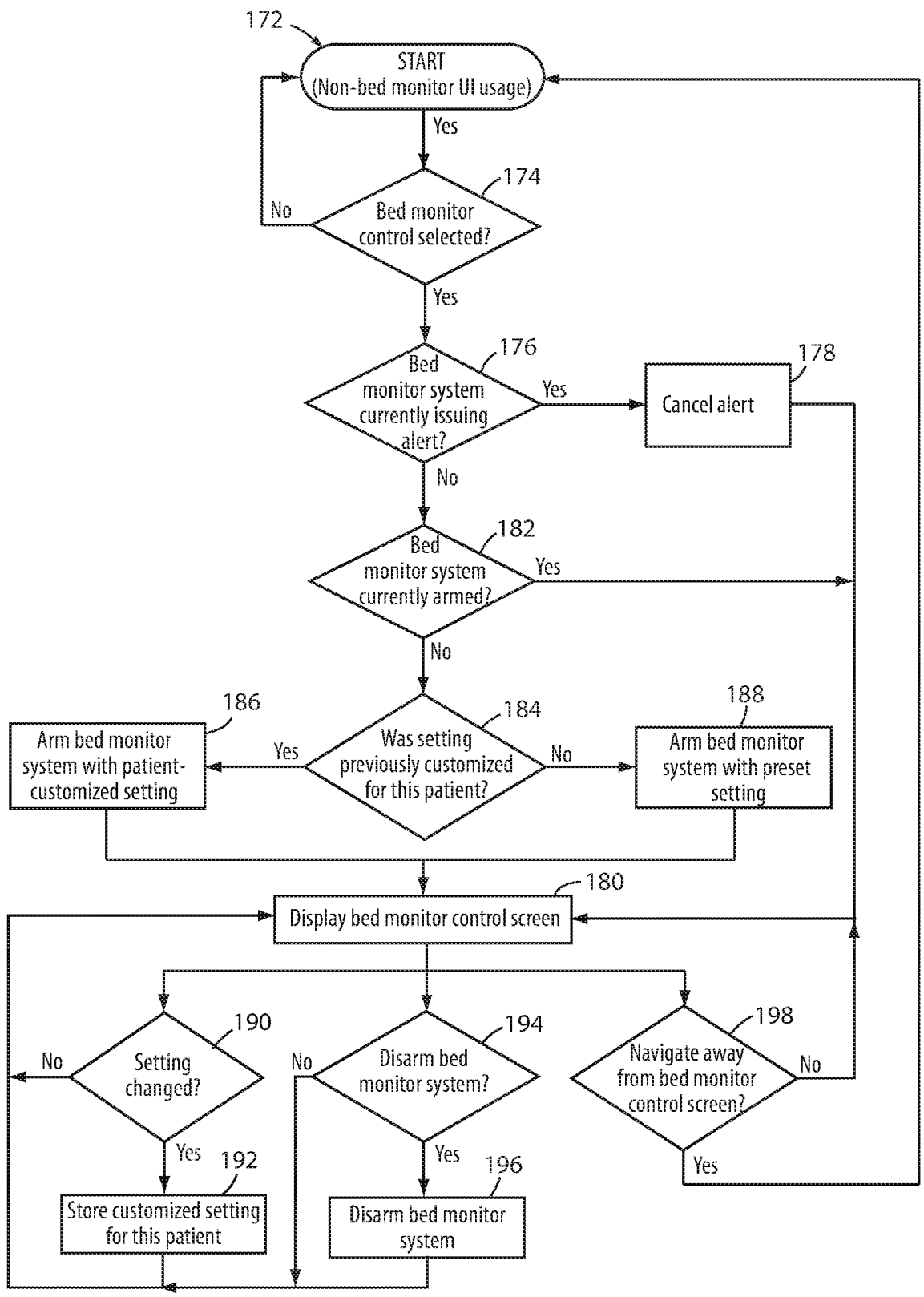
FIG. 8 is a bed monitor management algorithm executed by a controller of the user interface.

Controller 94 is also configured to not only automatically arm bed monitor system 104 in response to the user touching navigation control 66b, but it is also configured to automatically arm bed monitor system 104 using either a set of preset settings or a set of patient-customized settings that were previously selected by the caregiver for the particular patient who is now occupying patient support apparatus 30. These features are discussed in more detail below with respect to bed monitor management algorithm 172 (FIG. 8).

Referring first to FIG. 6, bed monitor control screen 110 includes an arm/disarm control 152 for disarming bed monitor system 104 (and manually arming bed monitor system 104 if it has been disarmed while screen 110 is displayed). Upon user-activation of the arm/disarm control 152, controller 94 disarms bed monitor system 104. Subsequent selection of the arm/disarm control 152 causes controller 94 to rearm bed monitor system 104.

Bed monitor control screen 110 includes setting controls 154a-g and associated setting indicators 156a-g for each of the conditions of patient support apparatus 30 which are able to be monitored by bed monitor system 104. Each setting control 154a-g corresponds to one of the monitorable conditions of bed monitor system 104. Setting control 154a corresponds to bed height; setting control 154b corresponds to side rail position for side rail 44; setting control 154c corresponds to side rail position for side rail 46; setting control 154d corresponds to side rail position for side rail 48; setting control 154e corresponds to side rail position for side rail 50; setting control 154f corresponds to head-of-bed (HOB) angle, which is shown herein as set for a 30 degree angle; and setting control 154g corresponds to bed tilt angle, which is shown herein as set for a flat bed (zero degree angle). Text and/or graphics, or other forms of visual content, are associated with the setting controls 154a-g to indicate which of the monitorable conditions correspond to which setting control.

The setting indicators 156a-g indicate the current setting of the monitorable conditions to the caregiver, e.g. whether the associated condition is currently being monitored or not monitored by bed monitoring system 104. Setting indicators 156a-g include a check mark when the associated condition is being monitored and do not include this check mark when the associated condition is not being monitored. In some embodiments, controller 94 displays an X mark (or some other non-check mark symbol) instead of the check mark when the condition is not being monitored, or leaves the interior of the setting indicator 156a-g blank when the condition is not being monitored. In addition to utilizing a symbol to convey which condition is being monitoring and which condition is not being monitored, controller 94 may also change the color of indicators 156a-g to indicate whether the monitored condition is currently in its desired state or its undesired state. When in the desired state, controller 94 may display the corresponding indicator 156a-g in green, and when in the undesired state, controller 94 may display the corresponding indicator 156a-g in amber, or some other color.

In the particular example shown in FIG. 6, the bed height and all of the side rails are being monitored, and their associated setting indicators 156a, 156b, 156c, 156d, and 156e include a check mark. The HOB angle is also being monitored but the current angle of back section 41 is below the desired threshold (the undesired state), so controller 94 is shown displaying an exclamation point in indicator 156f (and its color has changed to amber). The bed angle is not being monitored, and its associated setting indicator 156g is displayed without a check mark and in a gray color. The setting indicators 156a, 156b, 156c, 156d, 156e, 156f, 156g may alternatively employ text or graphics, or other forms of visual content, to indicate the current setting of the monitorable conditions.

When determining which color to display a particular setting indicator 156a-g, controller 94 uses the outputs from sensors 82-88 to determine if the corresponding monitored component is in a desired state or an undesired state. Thus, the color of setting indicators 156a-f are selected by controller 94 based at least in part on readings from the sensors 82, 84, 86, and 88. The color of setting indicator 156a is selected by controller 94 based at least in part on readings from height sensors 86; the colors of setting indicators 156b-e are selected by controller 94 based at least in part on readings from side rail sensors 82; the color of setting indicator 156f is selected by controller 94 based at least in part on readings from HOB angle sensor 84; and the color of setting indicator 156g is selected by controller 94 based at least in part on readings from the bed angle sensors 88.

Bed monitor control screen 110 also includes a home navigation control 66d and a menu navigation control 162 for navigating away from the bed monitor control screen 110. Upon user-activation of the home navigation control 66d, controller 94 is operable to display a home screen, which, in some embodiments, may be motion control screen 106 (FIG. 2), although other home screens may also be displayed on display 64a. Upon user-activation of menu navigation control 122, controller 94 is operable to display a menu screen (not shown) on display 64a.

Bed monitor control screen 110 also includes state controls 164a, 164f for selecting the desired state and/or undesired state for one or more of the conditions of patient support apparatus 30 which are monitorable via bed monitor system 104. Pressing the state control 164a, 164f allows the caregiver to change a threshold value for the monitored condition. For example, pressing HOB angle state control 164f switches the preset HOB angle between 30 degrees and 45 degrees (or in some cases, allows the user to select any numeric value for the minimum HOB angle). In FIG. 6, the threshold HOB angle is shown as being 30 degrees. Upon user-activation of the HOB angle state control 164f, controller 94 is operable to change the threshold HOB angle to 45 degrees. Subsequent selection of the HOB angle state control 164f changes the threshold HOB angle back to 30 degrees.

Figure 7:
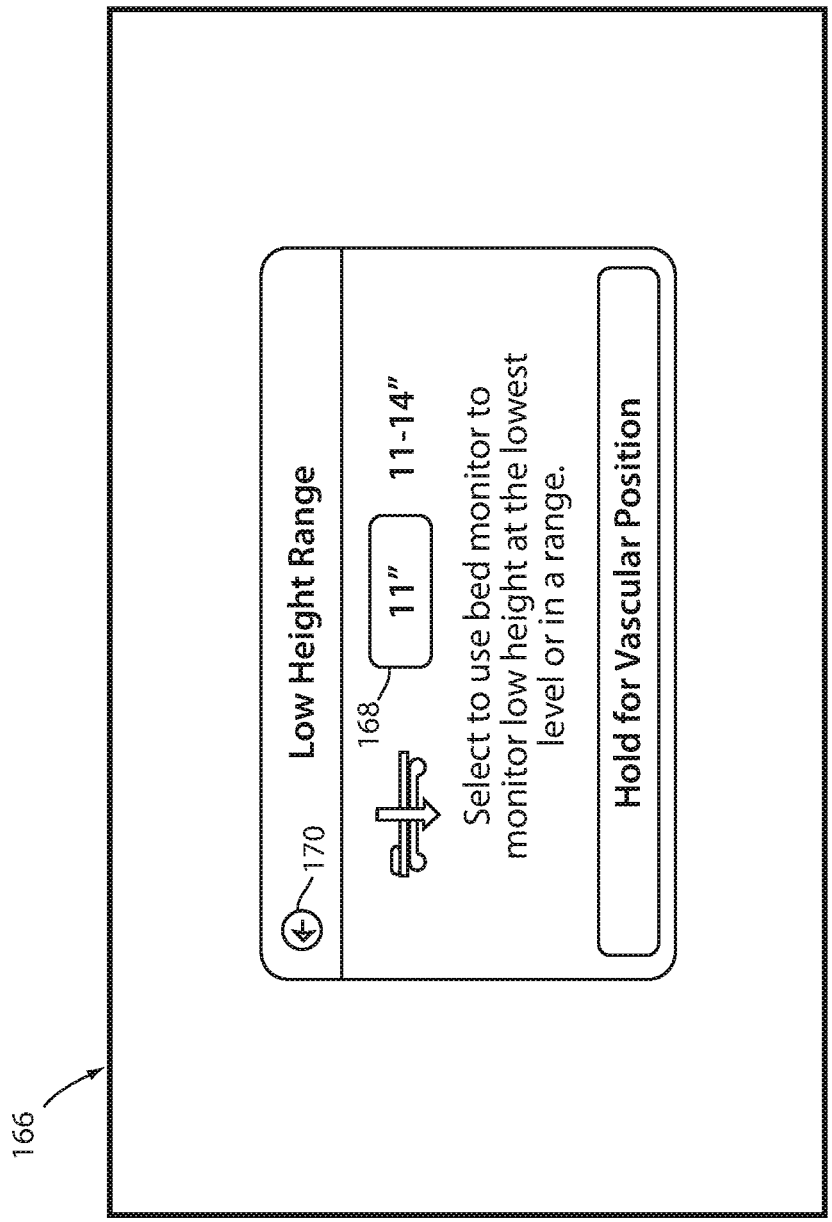
FIG. 7 is an illustrative state control screen that may be displayed on the display.

In some embodiments, pressing the state control 164a, 164f causes controller 94 to display a separate screen with controls for selecting the desired state and/or undesired state for each of the conditions. FIG. 7 shows a state control screen 166 that may be displayed on user interface 62 of FIG. 2 in response to the caregiver touching state control 164a. State control screen 166 is used by a caregiver or other user to select a threshold height which support frame 36 is desirably kept at or below (and which will trigger an alert when support frame 36 goes above). State control screen 166 includes a bed height state control 168 for selecting the desired threshold height which support frame 36 is desirably kept at or below. In this particular example, the desired threshold height can be chosen to be either a single height of eleven inches, or a range of heights between eleven and fourteen inches. If the caregiver selects eleven inches and then uses setting control 154a to include the bed height amongst the parameters monitored by bed monitoring system 104, controller 94 will issue an alert if the height of support frame 36 moves above eleven inches. If the caregiver selects the range of eleven to fourteen inches and then uses setting control 154a to include the bed height amongst the parameters monitored by bed monitoring system 104, controller 94 will issue an alert if the height of support frame 36 goes above fourteen inches. Of course, if the caregiver does not use setting control 154a to include the bed height amongst the parameters monitored by bed monitoring system 104, controller 94 will not issue any alerts based on the height of support frame 36, no matter how high it is raised or how low it is lowered.

In at least one embodiment, the particular height and angular values used for state controls 164a and 164f are customizable in any of the manners disclosed in commonly assigned U.S. patent application Ser. No. 62/783,442 filed Dec. 21, 2018, by inventors Kurosh Nahavandi et al. and entitled "Patient Support Apparatuses with Motion Customization," the complete disclosure of which is incorporated herein by reference.

When bed monitor navigation control 66b on user interface 62 is selected, controller 94 begins following a bed monitor management algorithm 172, one example of which is shown in FIG. 8. Bed monitor management algorithm 172 begins at step 174 when the bed monitor navigation control 66b is selected by the user. Prior to this, the caregiver can be using user interface 62 to perform another function and/or controller 94 may be displaying a different screen not associated with bed monitoring system 104. For instance, controller 94 may be displaying motion control screen 106 on display 64a at the moment the caregiver touches bed monitor navigation control 66b.

After bed monitor navigation control 66b is selected, controller 94 proceeds to step 176 where it determines if bed monitor system 104 is currently issuing an alert. Such an alert is issued if bed monitor system 104 is armed and one or more monitored conditions changes to an undesired state. If bed monitor system 104 is currently issuing an alert, controller 94 proceeds to step 178 and cancels the alert. For instance, in the case where the issued alert comprises projecting light from first light emitter 68 or second light emitter 78, controller 94 cancels the alert by deactivating these light emitters. In another example, controller 94 cancels the alert by changing the color, frequency, or illumination pattern of light projected from one or more lights, such as, but not limited to, first light emitter 68 and/or second light emitter 78. In another example, the issued alert comprises an audible sound emitted from a speaker, buzzer, or the like, and/or a message sent from patient support apparatus 30 to a remote device, and controller 94 can cancel the alert by silencing the audible alarm and/or sending an alert cancellation message to the remote device. After cancelling the alert, controller 94 proceeds to step 180 and displays bed monitor control screen 110 on display 64a.

If bed monitor system 104 is not currently issuing an alert, controller 94 proceeds from step 176 to step 182, where it determines if bed monitor system 104 is currently armed. If bed monitor system 104 is currently armed, controller 94 proceeds to step 180 and displays bed monitor control screen 110 on display 64a.

If bed monitor system 104 is not currently armed, controller 94 proceeds from step 182 to step 184 and determines whether a setting was previously customized for the patient currently assigned to patient support apparatus 30. If a setting was previously customized for the patient, the controller proceeds to step 186 and arms bed monitor system 104 with the patient-customized setting. If no setting was previously customized for the patient currently assigned to patient support apparatus 30, controller 94 proceeds from step 184 to step 188 where it arms bed monitor system 104 with a preset setting. From both steps 186 and step 188, controller 94 proceeds to step 180 where it displays bed monitor control screen 110.

Before turning to the operation of control screen 110, it should be noted that the patient-customized setting used in step 186 and the preset setting used in step 188 both refer to, in at least one embodiment, the set of conditions that are monitored by bed monitor system 104 when it is armed. Additionally, if the set of conditions includes the height of support frame 36 (activated by setting control 154a) the patient-customized setting and the preset setting include the specific threshold height that triggers an alert when support frame 36 is raised thereabove (e.g. eleven inches, fourteen inches, etc.) Further, if the set of conditions that are monitored by bed monitor system 104 includes the HOB angle, the patient-customized and preset settings includes the specific angle that triggers an alert when back section 41 is pivoted to less than this angle (e.g. forty-five degrees, thirty-degrees, etc.).

It will also be understood that, in addition to the specific set of conditions monitored by bed monitor system 104 (as well as the threshold values for the height of support frame 36 and the angle of back section 41), the setting referred to in steps 186 and 188 may refer to and/or include other settings associated with bed monitor system 104. For example, the setting referred to in steps 186 and 188 may relate to one or more characteristics of the alert that is issued when bed monitor system 104 is triggered, such as which lights, if any, are activated, what sounds, if any, are activated (and/or their volume level), and/or if the alert is to be communicated to a remote location and, if so, how such communication takes place and/or to what devices the communication is to be forwarded. Still other types of settings may be incorporated into steps 186 and 188.

In one embodiment, the preset setting used by controller 94 at step 188 is defined by the manufacturer of the patient support apparatus 30 and includes the following definition: (1) the position of all four side rails 44, 46, 48, and 50 are monitored and an alert is triggered if any of them is lowered; (2) the HOB angle is monitored and an alert is triggered if the angle of back section 41 pivots to less than the threshold HOB angle; (3) the state of the brake is monitored and an alert is issued if the brake is deactivated; and (4) the height of support frame 36 is monitored and an alert is issued if the height is raised above the threshold height. In this embodiment, if any one or more of these conditions are changed or omitted, or if any additional monitored conditions are added to these, such changes represent a patient-customized setting, which is stored in memory 100 and automatically implemented by controller 94 at step 186 in response to the user pressing bed monitor navigation control 66b.

From bed monitor control screen 110, the caregiver is able to arm and/or disarm bed monitor system 104 via arm/disarm control 152, as well as to change one or more of the settings via the setting controls 154a-g or state controls 164a, 164f. While the bed monitor control screen 110 is being displayed, controller 94 monitors user interface 62 to see if the caregiver activates one or more functions associated with screen 110, and follows steps 190 through 198 of algorithm 124.

If the caregiver makes any changes to the settings of bed monitor system 104 while bed monitor control screen 110 is displayed (e.g. selects an additional condition to be monitored, omits a condition to be monitored, and/or changes a threshold height or HOB angle), controller 94 not only implements those changes immediately for bed monitor system 104, but it also saves those changes in memory and uses them as patient-customized settings whenever bed monitor system 104 is armed in the future (at least for that same patient). In other words, setting controls 154a-g not only function as controls for changing the current settings of bed monitor system 104, but they also automatically customize those settings for the particular patient who is currently assigned to patient support apparatus 30.

For example, if a patient A is currently occupying patient support apparatus 30 and the caregiver arms bed monitor system 104 by touching navigation control 66b, controller 94 automatically arms bed monitor system 104 and displays bed monitor control screen 110. If this is the first time that bed monitor system 104 has been armed for patient A, controller 94 follows step 188 and arms bed monitor system 104 using the preset setting which, in at least one embodiment, refers to monitoring the four components mentioned above (e.g. siderail position, HOB angle, brake status, and support frame 36 height). After arming bed monitor system 104 such that these four conditions are monitored at step 188, controller 94 displays bed monitor control screen 110 and allows the user to change any of these conditions, and/or the threshold height or threshold HOB angle via controls 164a and 164f, respectively.

If the user selects, say, control 154a such that the check mark is no longer displayed as part of indicator 156a, controller 94 omits the height of support frame 36 from the list of conditions that are monitored by bed monitor system 104 when it is armed. Further, controller 94 also stores this omitted support frame height monitoring in memory and automatically uses it for all the future times it arms bed monitor system 104 for patient A. Thus, if bed monitor system 104 is later disarmed (say, while patient A exits from patient support apparatus 30 and subsequently returns), and bed monitor system 104 is re-armed with patient A onboard, controller 94 will follow step 186 of algorithm 172 and automatically re-arm the bed monitor system such that it does not monitor the height of support frame 36. In this manner, once a caregiver selects a condition to be omitted from monitoring for a particular patient, every time the caregiver re-arms bed monitor system 104 with that particular patient onboard, controller 94 automatically omits the condition from those that are monitored by bed monitor system 104. The same is true for added conditions: once they are added for a particular patient, every time the caregiver re-arms bed monitor system 104, the added condition is automatically monitored in response to the user pressing the single navigation control 66b.

Bed setting controls 154a-g therefore not only change the current conditions being monitored by bed monitor system 104, but they also define the patient-customized setting for future usage of bed monitor system 104 with that particular patient. Still further, if a caregiver has already customized one or more settings for bed monitor system 104 for a particular patient, he or she can use setting controls 154a-g to change the previous customization for that particular patient. This is done by merely touching one or more of the setting controls 154a-g and changing their corresponding condition from one that is monitored to one that is not monitored, or vice versa. The same is true for controls 164a and 164f.

This process of customizing the monitored conditions of bed monitor system 104 for a particular patient is illustrated in steps 190 and 192 of algorithm 172 (FIG. 8). If the caregiver makes any changes to the monitored conditions via bed monitor control screen 110, such as by selecting one of the setting controls 154a-g or state controls 164a, 164f, controller 94 moves to step 190 and implements those changes for bed monitor system 104. Controller 94 then moves to step 192 where it stores the new patient-customized setting for the patient in memory 100 and sets (or resets) the patient-customized setting to match the recorded change. As a result, the next time controller 94 executes step 184, it will proceed to step 186 and implement the patient-customized setting that was stored previously at step 192.

If the caregiver presses the arm/disarm control 152 on the bed monitor control screen 110 at step 146, controller 94 moves to step 194 where it disarms bed monitor system 104. After disarmament of bed monitor system 104, controller 94 continues to display bed monitor control screen 110 on display 64a. In some embodiments, controller 94 changes the label on arm/disarm control 152 from "turn off" to "turn on" after the caregiver has disarmed bed monitor system 104 and toggles these two labels back and forth as the caregiver switches between arming and disarming bed monitor system 104. Alternatively, after disarmament of bed monitor system 104, controller 94 may be configured to display a different screen on display 64a, such as motion control screen 106 of FIGS. 2 and 3, or another screen (not shown). In one example, controller 94 displays a confirmation screen on display 64a which confirms that bed monitor system 104 has been disarmed, after which controller 94 displays bed monitor control screen 110, motion control screen 106, or another screen (not shown) on display 64a.

If the caregiver navigates away from the bed monitor control screen 110, such as by selecting the home navigation control 66d or the menu navigation control 162 on the bed monitor control screen 110 at step 198, controller 94 returns to the start of the algorithm 172 the next time bed monitor navigation control 66b is touched.

It will be understood that, in some embodiments, the preset setting used at step 188 is set by the manufacturer of patient support apparatus 30 and cannot be changed. It will also be understood that, in some alternative embodiments, patient support apparatus 30 can be constructed in a manner that allows healthcare administrators, or other authorized personnel, to change the preset setting used at step 188. In these latter embodiments, healthcare administrators can override the factory-defined preset setting and choose a different preset setting that better suits their particular needs. However, even if the healthcare facility decides to change the preset setting to one that better suits their needs, the caregiver can still customize this setting to a particular patient in the manner just described. The following table illustrates one example of factory-defined preset setting, a healthcare facility-defined preset setting, and a patient-customized setting.

| Preset Setting for Bed Monitor System 104 | | Patient-Customized Setting for Bed Monitor System 104 |
|---|---|---|
| Factory-Defined | Healthcare Facility-Defined | |
| All four siderails monitored | All four siderails monitored | All four siderails monitored |
| HOB angle monitored (≤45°) | HOB angle monitored (≤45°) | HOB angle monitored (≤30°) |
| Brake status monitored | Brake status monitored | Brake status monitored |
| Support frame height monitored | Support frame height monitored | Support frame height monitored |
| | Exit detection system monitored | Exit detection system monitored |

In the particular example shown in this table, patient support apparatus 30 is manufactured such that, unless changed by the healthcare facility or caregiver, controller 94 will arm bed monitor system 104 in response to activation of bed monitor navigation control 66b to monitor all four siderails, the HOB angle for angles less than or equal to 45 degrees, the brake, and the height of support frame 36 for heights less than or equal to the threshold height. If any of these four conditions change to an undesired state, bed monitor system issues an alert.

If the healthcare facility that purchases patient support apparatus 30 does not wish to continue to use the factory-defined preset settings shown above, the healthcare facility—in at least one embodiment—can change these preset settings. One manner in which these preset settings can be changed is discussed in more detail below with respect to FIG. 11. In the example shown above in the table, the healthcare facility has changed the preset setting to add the exit detection system 102 to the list of conditions that are monitored by bed monitor system 104. When modified in this manner, bed monitor system 104 will issue an alert any time the exit detection system 102 is disarmed (while bed monitor system 104 is armed). This helps ensure that the exit detection system 102 is armed at the appropriate times.

If the caregiver does not wish to utilize either the factory-defined preset setting or the healthcare facility-defined preset setting for a particular patient, he or she can customize the settings of bed monitor system 104 by using setting controls 154a-g in the manner described above. In the example shown in the table above, the caregiver has changed the healthcare facility-defined settings by changing the HOB angle from forty-five degrees to thirty degrees. Other changes can, of course, be made both by the caregiver and by the healthcare facility.

It will also be understood that various changes may be made to bed monitor management algorithm 172 from the particular implementation shown in FIG. 8, such as changing the order of one or more steps, adding one or more additional steps, omitting one or more of the existing steps, and/or modifying one or more of the existing steps. In one such example, the particular order of step 180 is changed such that it occurs earlier than shown, such as between step 174 and step 176. Still other locations of step 180 within algorithm 172 may also be implemented.

Patient support apparatus 30 includes a new patient function that allows the caregiver to erase old parameters, including any patient-customized settings, of patient support apparatus 30 that were previously stored for a previous patient. The new patient function is therefore activated when a new patient is to be assigned to patient support apparatus 30 and the old data (stored in memory 100) associated with the previous patient is desirably erased. In addition to erasing old data, the new patient function resets any patient-customized settings for the exit detection and/or bed monitor systems 102, 104 to their preset setting. The resetting of any patient-customized settings to their preset settings refers to either the factory-defined preset setting or the healthcare facility-defined preset setting. That is, if the healthcare-facility has never changed the factory-defined preset setting, the new patient function resets the patient-customized settings to the factory-defined preset settings. On the other hand, if the healthcare-facility has changed one or more of the factory-defined preset settings, the new patient function resets the patient-customized settings to the healthcare facility-defined preset settings.

The new patient function is activated via a new patient control 200 that is displayed on one or more screens, such as, but not limited to, motion control screen 106 (FIG. 2). When the caregiver presses the new patient control 200, controller 94 displays a new patient control screen on display 64a, such as the new patient control screen 202 shown in FIG. 9. New patient control screen 202 includes a reset control 204 and a cancel control 206, and a confirmation message requesting that the caregiver confirms that a new patient should be entered and all previous patient data should be erased. Upon user-activation of the reset control 204, controller 94 erases all previous patient data stored in the memory 100, including any patient-customized settings for the exit detection and/or bed monitor systems 102, 104. Upon user-activation of the cancel control 206, controller 94 displays motion control screen 106 (or another screen) on display 64a, and does not erase any patient data stored in the memory 100.

The new patient control screen 202 also includes a return control 208 for returning to motion control screen 106 (FIG. 2), or whatever screen was previously displayed before arriving at new patient control screen 202. Upon user-activation of the return control 208, controller 94 displays motion control screen 106 on display 64a, or whatever screen was previously displayed.

Figure 10:
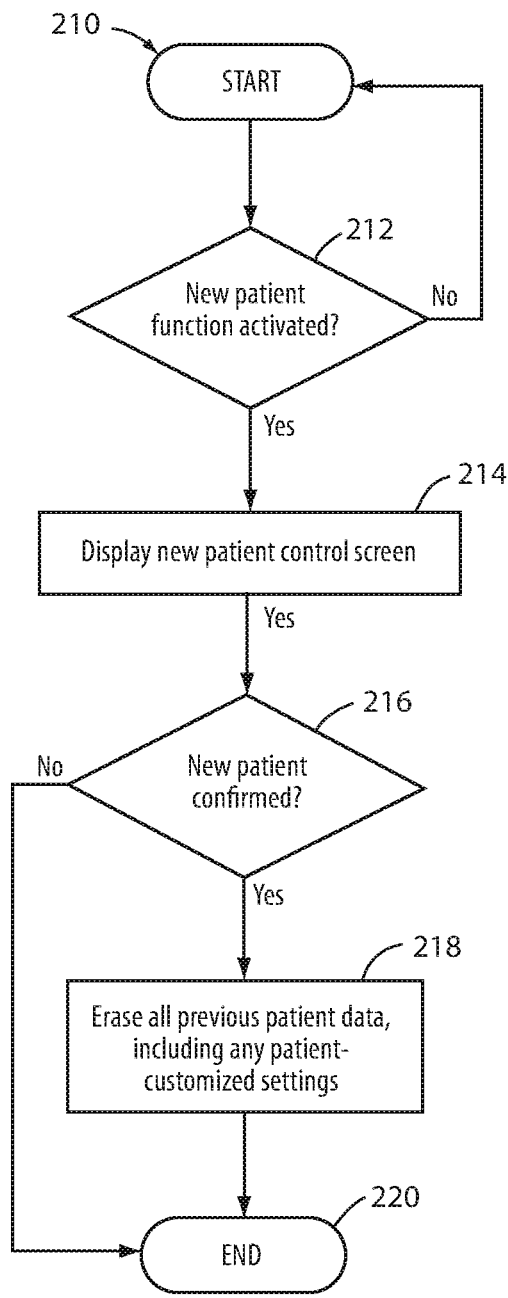
FIG. 10 is a new patient function algorithm executed by the controller of the user interface.

When the new patient function is activated, controller 94 begins following a new patient algorithm 210, one example of which is shown in FIG. 10. New patient algorithm 210 begins at step 212 when the new patient function is activated by the caregiver. Prior to this, the caregiver may be using user interface 62 to perform other functions and/or controller 94 may be displaying other screens on display 64a.

Figure 9:
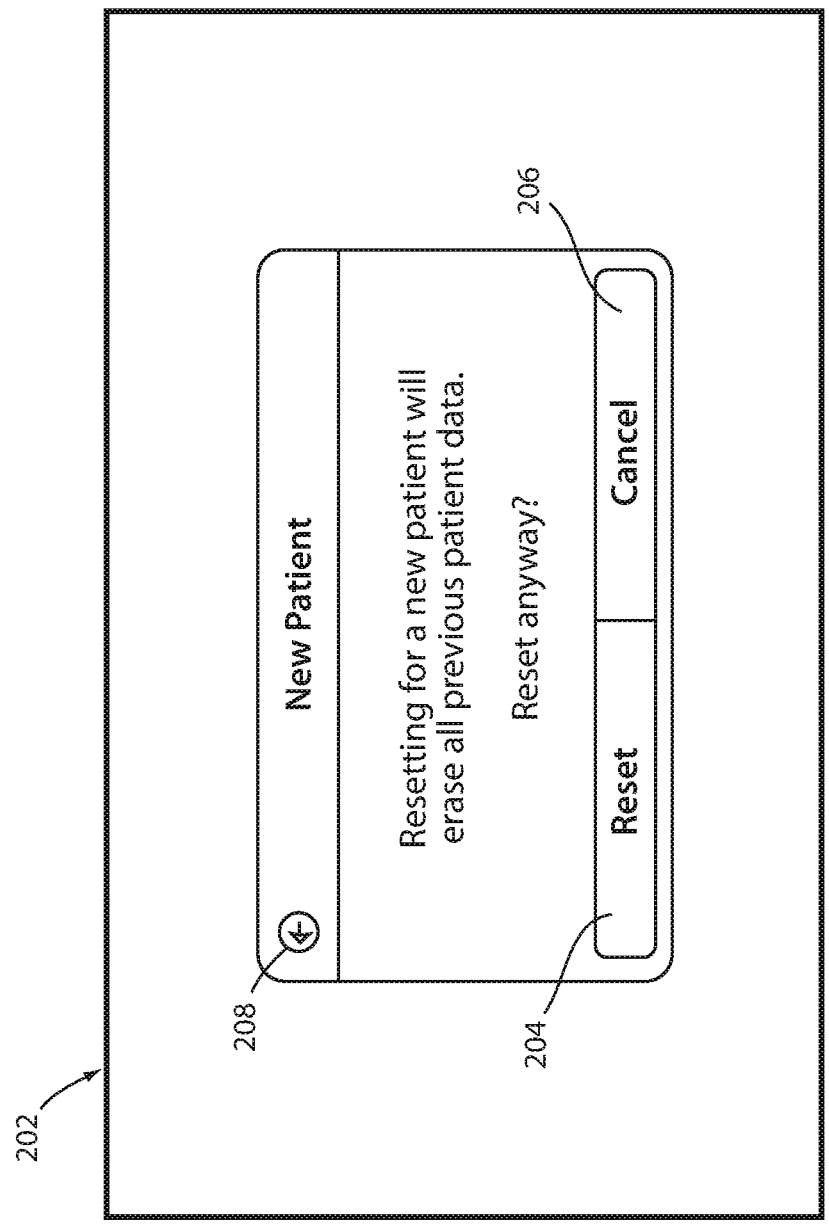
FIG. 9 is an illustrative new patient control screen that may be displayed on the display.

New patient algorithm 210 (FIG. 10) begins at step 212 where controller 94 determines if the caregiver has activated (e.g. touched) new patient control 200, or otherwise navigated to the new patient control screen 202 (FIG. 9). If either of these conditions are met, controller 94 displays new patient control screen 202 at step 214. While displaying new patient control screen 202, controller 94 determines if the caregiver has selected "reset" control 204, "cancel" control 206, or "back" control 208. If the caregiver selects "reset" control 204, controller 94 interprets this as confirmation of the caregiver's intent at step 216 and proceeds to step 218 where it erases all of the patient-customized settings and returns to using the preset settings the next time exit detection navigation control 66a or bed monitor navigation control 66b is touched. In some embodiments, the erasure at step 218 is a complete erasure of the patient-customized settings such that this data cannot be subsequently retrieved, while in other embodiments the erasure involves resetting patient support apparatus 20 to the healthcare-facility settings while saving a copy of the patient-customized settings for later retrieval, if desired. If the caregiver selects "cancel" control 206 or "back" control 208, controller 94 retains the patient-customized settings, stops algorithm 210, and returns to displaying on display 64a whatever screen it was previously displaying before it started algorithm 210.

As mentioned previously, the new patient function does not erase any healthcare facility-defined preset settings, only the patient-customized settings. Thus, in the example shown in the table above, activating the new patient function will cause bed monitor system to switch back to monitoring the HOB angle for angles less than or equal to forty-five degrees. It will not, however, omit the monitoring of exit detection system 102, and therefore will not return bed monitor system 104 to the state in which it was originally defined by the manufacturer of patient support apparatus 30.

As was also previously mentioned, user interface 62 can be provided with one or more screens that enable the healthcare facility to change the factory-defined preset settings into one or more healthcare-facility defined preset settings. Such changes allow the healthcare facility to change the preset settings for the exit detection and/or bed monitor systems 102, 104, and thus allow the caregiver to change, for example, the preset sensitivity level for exit detection system 102, the preset set of monitored conditions for bed monitor system 104, and/or the preset desired and undesired states for one or more of the monitorable conditions of bed monitor system 104. The updated preset settings are thereafter applied for all new patients until—and if—the caregiver customizes one or more of these preset settings for a particular patient.

For bed monitor system 104, the changing of the factory-defined presets may be carried out by touching a menu control 222 (see, e.g. FIG. 2) that causes controller 94 to display a main menu of control options (not shown). One of the control options is an option for changing the settings of patient support apparatus 30. When that setting-changing option is selected, controller 94 is configured, in at least one embodiment, to display a screen like the bed monitor presets control screen 224 shown in FIG. 11.

Bed monitor presets control screen 224 (FIG. 11) includes preset controls 226a-g and associated preset indicators 228a-g for each of the conditions of patient support apparatus 30 which are monitorable via bed monitor system 104. Each preset control 226a-g corresponds to one of the monitorable conditions of bed monitor system 104. Preset control 226a corresponds to the height of support frame 36; preset control 226b corresponds to the position of side rail 44; preset control 226c corresponds to the position of side rail 46; preset control 226d corresponds to the position of side rail 48; preset control 226e corresponds to the position of side rail 50; preset control 226f corresponds to the head-of-bed (HOB) angle, which is shown herein as set for a 30 degree angle; and preset control 226g corresponds to the bed tilt angle, which is shown herein as set for a flat bed angle (zero degrees). Text and/or graphics, or other forms of visual content, are associated with the preset controls 226a-g to indicate which of the monitorable conditions correspond to which preset control.

Controller 94 displays each preset control 226a-g with a check mark if the condition associated with that control is one of the conditions that bed monitor system 104 is currently configured to monitor. If a control is not currently configured to be monitored by bed monitor system 104, controller 94 may display the corresponding preset controls 226a-g with an X, some other symbol, or no symbol at all. Each preset control 226a-g is set to toggle between a monitored condition and an unmonitored condition. Thus, in the example shown in FIG. 11, the preset settings for bed monitor system 104 include all of the monitorable conditions: bed height, all of the siderails, HOB angle, and bed tilt. If the caregiver wishes to exclude one or more of these conditions, he or she simply touches the preset control(s) 226a-g that correspond to the condition(s) that are to be omitted from monitoring. In some embodiments, controller 94 is configured to display preset controls 226a-g in different colors, depending upon whether the associated condition is selected for monitoring or not.

Figure 11:
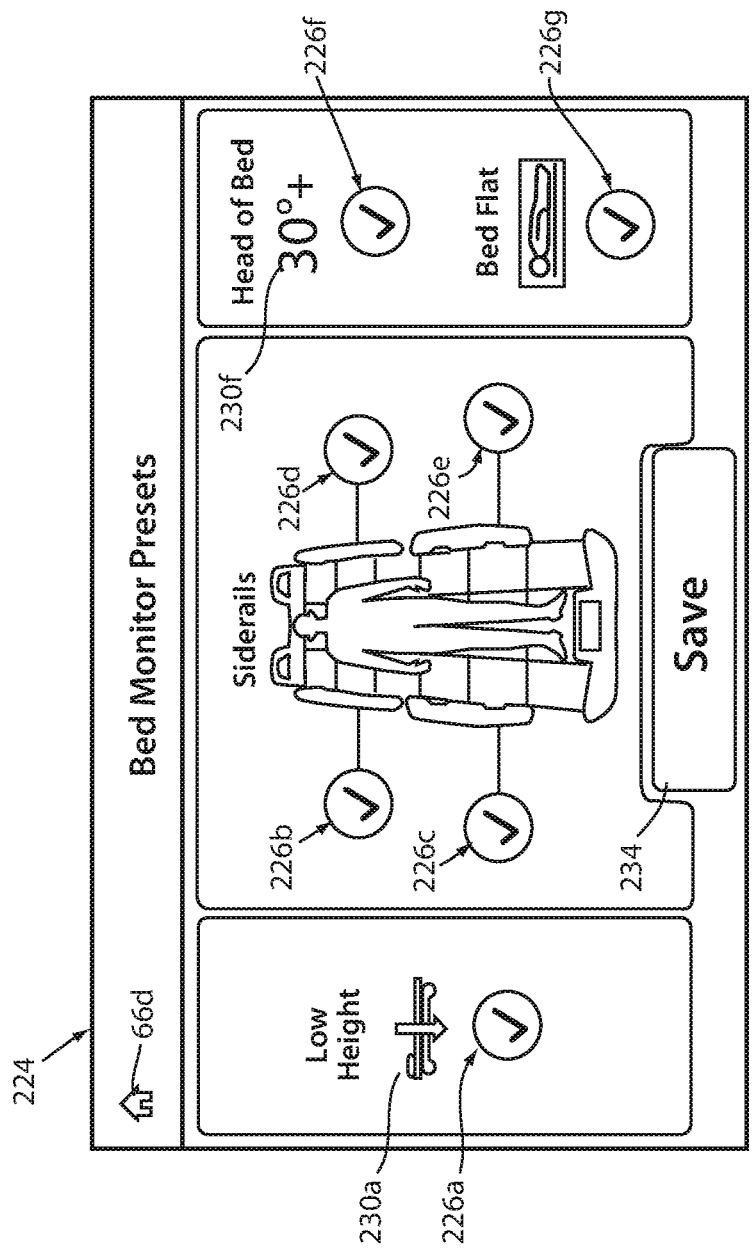
FIG. 11 is an illustrative bed monitor presets control screen that may be displayed on the display.

Bed monitor presets control screen 224 also includes preset state controls 230a, 230f for selecting the preset desired state for one or more of the conditions of patient support apparatus 30 which are monitorable via bed monitor system 104. Pressing the preset state control 230a, 230f allows the caregiver to change the particular threshold value that is used for the monitored condition. For example, pressing bed height preset state control 230a switches the default preset bed height between a lowest height of 11 inches and a lowest height range of 11-14 inches. Pressing HOB angle state control 230f switches the default preset HOB angle between 30 degrees and 45 degrees. In FIG. 11, the default preset HOB angle is shown as being 30 degrees. Upon user-activation of the HOB angle preset state control 230f, controller 94 is operable to change the default preset HOB angle to 45 degrees. Subsequent selection of the HOB angle preset state control 230f changes the default preset HOB angle back to 30 degrees.

Bed monitor presets control screen 224 further includes a save control 234 that saves the current settings to memory 100. Upon user-activation of the save control 234, controller 94 is operable to update the preset settings in the memory 100.

It will be understood that the particular set of monitorable conditions shown on screen 224 may be modified from what is illustrated in FIG. 11. In at least one embodiment, bed monitor system 104 is configurable to monitor whether exit detection system 102 is armed or disarmed, and to issue an alert if it is disarmed. In this embodiment, bed monitor presets control screen 224 may include an additional preset control 226 that corresponds to exit detection system 102, thereby enabling the user to selectively include or omit the exit detection system 102 from the list of items monitored by bed monitor system 104. Still other changes may be made to bed monitor presets control screen 224.

To the extent not already described, the different content and functions of the various systems and control screens of patient support apparatus 30, including the various embodiments of the exit detection system, the bed monitor system, and associated control screens and control methods disclosed herein, may be used in combination with each other as desired, or separately implemented. The content and/or functions of one control screen may be applied to one or more other control screen. Further, the selected content shown in any particular control screen herein is not to be construed that it must have all of the content shown therein.

It will be understood that, although exit detection navigation control 66a and bed monitor navigation control 66b have both been illustrated in the accompanying drawings as touchscreen controls that are positioned on display 64a, either or both of these controls could be controls that are physically separate from display 64a, such as one or more dedicated buttons, switches, or other controls. Alternatively, user interface 62 could be modified to include both navigation controls 66*a-b* on display 64*a* and one or more of physically separate navigation controls 66*a-b*.

FIGS. 12-15 illustrate a display lockout feature that may be incorporated into patient support apparatus 30. This display lockout feature may be incorporated into an embodiment of a patient support apparatus 30 that includes one or more of the various exit detection functions, bed monitor functions, and/or associated control screens and control methods disclosed herein and discussed above, or it may be separately incorporated into an embodiment of a patient support apparatus 30 that does not include any or all of the exit detection functions, bed monitor functions, and/or associated control screens and methods disclosed herein and discussed above. Thus, the display lockout features discussed herein may be implemented on a patient support apparatus separately and independently from the other features disclosed herein, or they may be implemented in combination with one or more of the other features disclosed herein.

The display lockout feature of FIGS. 12-15 allows a caregiver to lock out the usage of display 64*a* so that unauthorized users, such as visitors, are less likely to use any of the control functions that are accessible via display 64*a*. The display lockout feature is implemented with a display lockout indicator 300 that controller 94 adds to one or more of the control screens displayed on display 64*a*. In some embodiments, lockout indicator 300 is added to all of the control screens that are displayable on display 64*a*. In other embodiments, lockout indicator 300 is added to only one or another subset of the set of all screens that are displayable on display 64*a*.

Figure 12:
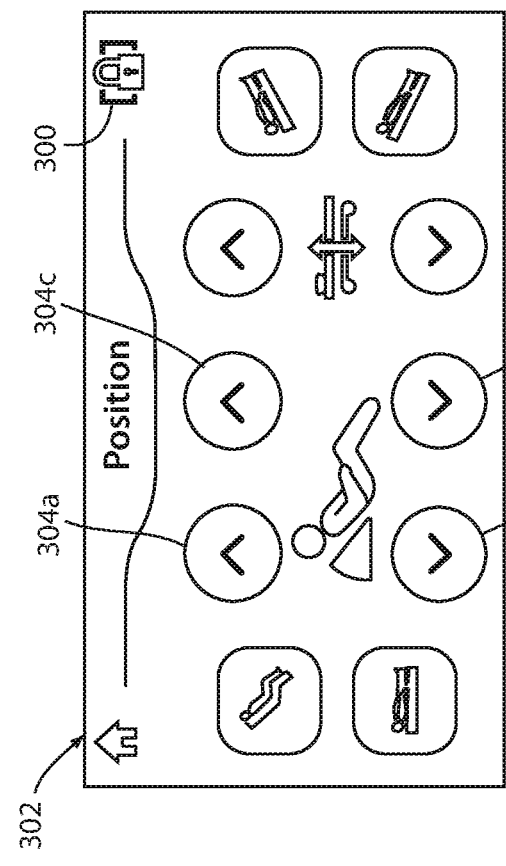
FIG. 12 is an illustrative motion control screen with a lock indicator that may be displayed on the display.

One example of the lockout indicator 300 is shown in FIG. 12. FIG. 12 illustrates a motion control screen 302 having a plurality of motion controls 304 for controlling movement of various portions of patient support apparatus 30. For example, motion control screen 302 includes a first motion control 304*a* for raising the back section 41 of patient support apparatus 30; a second motion control 304*b* for lowering the back section 41, a third motion control 304*c* for raising the patient's knees, and a fourth motion control 304*d* for lowering the patient's knees. Motion control screen 302 also includes other controls for controlling still other components of patient support apparatus 30. Motion control screen 302 is alternative variation of the motion control screen of 106 of FIG. 2 and it has been provided herein to illustrate one example of the different types of motion control screens that may be incorporated into patient support apparatus 30. In practice, patient support apparatus 30 will typically only include a single type of motion control, which may be screen 106, screen 302, or another variation. It will be understood that any or all of the functions of motion control screen 106 described above may be incorporated into screen 302, and that any of the lock out functions of screen 302 described below may be incorporated into motion control screen 106.

When the user wishes to lock out display 64*a* such that the controls displayed thereon—such as, but not limited to, motion controls 304 and/or 107—are no longer functional, he or she presses the lockout indicator 300. In response to the user pressing lockout indicator 300, controller 94 switches to displaying another screen, such as the first locking control screen 310 of FIG. 13. First locking control screen 310 includes lockout indicator 300 as well as an instruction 312 instructing the user to press and hold the lockout indicator 300 if the user wishes to continue with the process of locking out the functionality of display 64. If the user continues with the process of locking out display 64*a* by pressing and holding lockout indicator 300 on screen 310, controller 94 switches to displaying another screen, such as second locking control screen 320 of FIG. 14.

Figure 13:
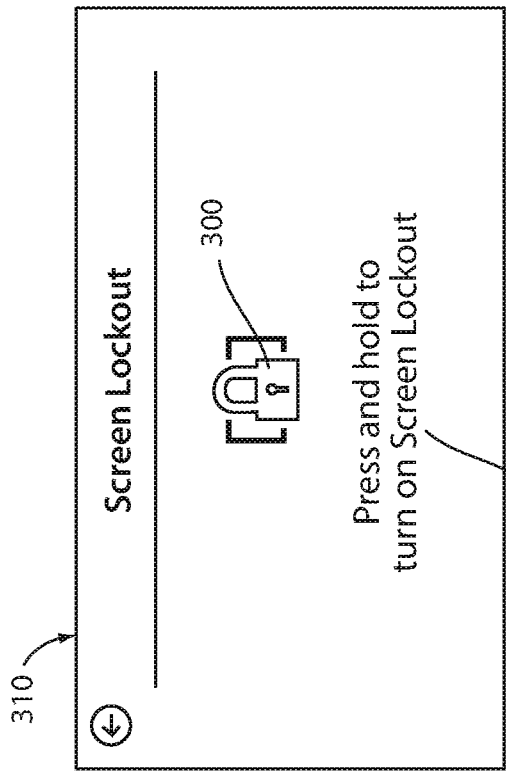
FIG. 13 is an illustrative first locking control screen that is displayed on the display in response to the user selecting the lock indicator of FIG. 12.
Figure 14:
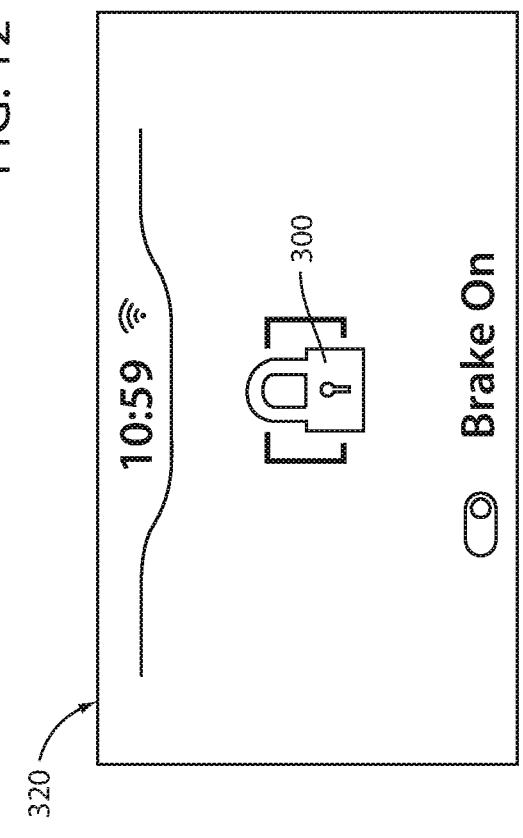
FIG. 14 is an illustrative second locking control screen that is displayable on the display in response to the user selecting and holding the lock indicator of FIG. 13.

Second locking control screen 320 of FIG. 14 includes lockout indicator 300, but controller 94 has displayed lockout indicator 300 in FIG. 14 in a different color from the color in which it is displayed in FIG. 13. The particular color variations may selected as desired, but in one embodiment, controller 94 displays lockout indicator 300 in white in FIG. 13 and in amber in FIG. 14. The color change provides an indication to the user that his or her pressing and holding of lockout indicator 300 is being detected and processed.

Figure 15:
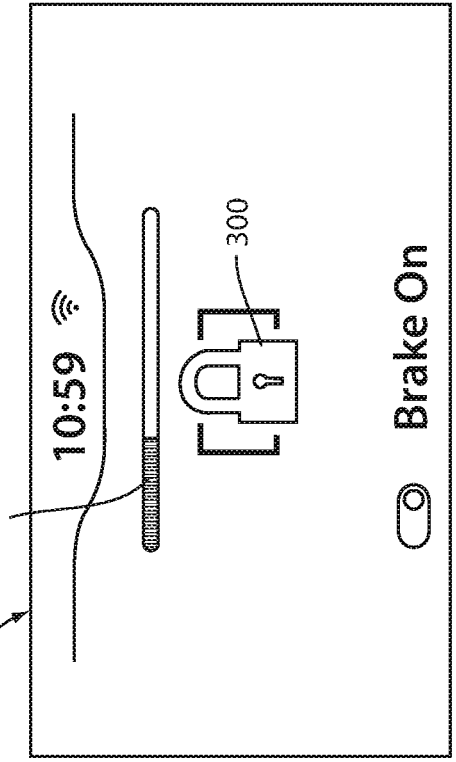
FIG. 15 is an illustrative third locking control screen that is displayable on the display in response to the user continuing to select and hold the lock indicator of FIGS. 13 and 14.

If the user continues to press and hold lockout indicator 300 on second locking control screen 320, controller 94 adds a progress bar 332 on the display, such as the progress bar 332 shown in FIG. 15. Progress bar 332 includes a progress indicator 334 initially fills none of progress bar 332, but gradually expands and fills more and more of progress bar 332 until, if the user continues to press and hold lockout indicator 300, it eventually fills the entirety of progress bar 332. Once the entirety of progress bar 332 has been filled by progress indicator 334, controller 94 locks out display 64*a*.

The locking out of display 64*a* may take on different forms. In one embodiment, controller 94 is configured to show a blank screen (such as, but not limited to, a black screen) on display 64*a* when it is locked out. In another embodiment, controller 94 is configured to show any or all of the screens that it normally displays, such as, but not limited to, motion control screen 302, but the functionality of those screen(s) is locked out. For example, if controller 94 were to display motion control screen 302 in this embodiment while display 64*a* was locked out, then the user pressing on any of controls 304*a-d* would not cause any movement of any components of patient support apparatus 30. Instead, controller 94 would ignore the activation of these controls and would continue to ignore such activations until display 64*a* was no longer locked out. As another example, if the user navigated to screen 110 (FIG. 6), the user would be able to view the settings shown there, but would not be able to change any of these settings until display 64*a* was unlocked. The same principle may be applied to still other screens that are displayable on display 64*a*.

In at least one embodiment, controller 94 is configured to allow the user to unlock display 64*a* in the same manner that it allows the user to lock the screen. That is, the user presses and holds lockout indicator 300 until progress bar 332 is completely filled by progress indicator 334, at which point controller 94 unlocks display 64*a*. Once unlocked, controller 94 restores the functionality of all of the controls (such as, but not limited to, controls 304) that appear on the various screens of display 64*a*. In some embodiments, controller 94 may be configured to display lockout indicator 300 in different colors, depending upon whether display 64*a* is locked out or not, thus providing an easily understood visual indication to the user of the lock status of display 64*a*.

The screen lock out process disclosed herein may be modified in a number of different manners from what has been discussed above with respect to FIGS. 12-15. For example, in some embodiments, controller 94 uses a circular progress bar instead of the linear progress bar 332 of FIG. 15. Other shapes may also or alternatively be used. Alternatively, the progress bar 332—regardless of its shape— may be omitted and controller 94 may be configured to display only the progress indicator 334. In still other embodiments, a pass code, a fingerprint, a pre-designated swiping motion, a series of line segments or other sketching, or still some other types of user-action may be required for the user to lock and unlock the display 64*a*, and such action(s) may take place either with or without a progress bar 332 and/or progress indicator 334.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
   a support structure including a patient support surface adapted to support a patient thereon;
   an exit detection system configured to be armed and disarmed, the exit detection system adapted to issue an alert when exit detection system is armed and the patient exits the patient support surface;
   a user interface comprising a display and an exit detection navigation control; and
   a controller operably coupled to the user interface, the controller configured to, in response to user-activation of the exit detection navigation control:
   display an exit detection control screen on the display, the exit detection control screen including a first control for setting a first sensitivity level of the exit detection system and a second control for setting a second sensitivity level of the exit detection system;
   determine whether the first sensitivity level or the second sensitivity level was previously used with a particular patient currently assigned to the patient support apparatus;
   arm the exit detection system with the first sensitivity level if the first sensitivity level was previously used with the particular patient;
   arm the exit detection system with the second sensitivity level if the second sensitivity level was previously used with the particular patient; and
   arm the exit detection system with a default sensitivity level if the exit detection system was not previously used with the particular patient.

2. The patient support apparatus of claim 1, wherein the exit detection navigation control is separate from the display.

3. The patient support apparatus of claim 1, wherein the controller is further configured to, in response to user-activation of the exit detection navigation control, determine if the exit detection system is currently issuing the alert, and to cancel the alert if the exit detection system is determined to be currently issuing the alert.

4. The patient support apparatus of claim 1 wherein the controller is further adapted to perform the following in response to a subsequent user-activation of the exit detection navigation control: re-display the exit detection control screen on the display, and arm the exit detection system with whichever sensitivity level was previously used for the particular patient.

5. The patient support apparatus of claim 1 wherein each sensitivity level corresponds to a particular zone, the exit detection system comprises a plurality of force sensors adapted to detect a center of gravity of the patient, and the exit detection system is configured to issue the alert if the patient's center of gravity moves outside of the particular zone.

6. The patient support apparatus of claim 1 further comprising a memory onboard the patient support apparatus in which the sensitivity level previously used with the particular patient is stored, and wherein the user interface includes a new patient control and the controller is further configured to erase the sensitivity level previously used with the particular patient from the memory in response to user-activation of the new patient control, but retain the default sensitivity level in the memory.

7. The patient support apparatus of claim 1 wherein the controller is further adapted to perform the following:
   arm the exit detection system with the first sensitivity level in response to the user activating the first control, regardless of which sensitivity level was previously used with the particular patient; and
   arm the exit detection system with the second sensitivity level in response to the user activating the second control, regardless of which sensitivity level was previously used with the particular patient.

8. A patient support apparatus comprising:
   a support structure having a patient support surface adapted to support a patient thereon;
   a monitoring system configured to be armed and disarmed, the monitoring system adapted to monitor a set of conditions of the patient support apparatus and to generate an alert when the monitoring system is armed and at least one condition from the set of conditions changes from a desired state to an undesired state;
   an exit detection system configured to be armed and disarmed, the exit detection system adapted to issue an exit alert when exit detection system is armed and the patient exits the patient support surface;
   a user interface comprising a display and a monitor navigation control; and
   a controller operably coupled to the user interface, the controller being configured to, in response to user-activation of the monitor navigation control: display a monitoring control screen on the display; determine whether a setting of the monitoring system was previously customized for the patient; and arm the monitoring system with the patient-customized setting if the setting was previously customized for the patient or with a preset setting if the setting was not previously customized for the patient.

9. The patient support apparatus of claim 8, wherein the monitor navigation control is separate from the display, the controller is further configured to, in response to user-activation of the monitor navigation control, determine if the monitoring system is currently issuing the alert, and to cancel the alert if the monitoring system is determined to be currently issuing the alert, and the patient-customized setting defines what conditions are in the set of conditions monitored by the monitoring system.

10. The patient support apparatus of claim 8 wherein the monitoring control screen includes a plurality of monitoring controls and each monitoring control corresponds to a particular condition of the patient support apparatus, wherein the controller is configured to change the set of conditions monitored by the monitoring system based on whether the user activates one or more of the monitoring controls or deactivates one or more of the monitoring controls.

11. The patient support apparatus of claim 10 wherein the controller is further configured to automatically adjust the patient-customized setting in response to the user activating one or more of the monitoring controls or deactivating one or more of the monitoring controls, and the controller is further configured to perform the following in response to a subsequent user-activation of the monitor navigation control: display the monitoring control screen on the display, and arm the monitoring system with the adjusted patient-customized setting.

12. The patient support apparatus of claim 8 wherein the set of conditions monitored by the monitoring system includes at least two of the following: a height of the patient support surface, a state of a brake onboard the patient support apparatus, a position of one or more siderails onboard the patient support apparatus, an armed/disarmed state of the exit detection system, and an angle of a pivotable back section of the patient support surface.

13. The patient support apparatus of claim 8 wherein the patient-customized setting also defines a desired state for at least one of the conditions in the set of conditions monitored by the monitoring system.

14. The patient support apparatus of claim 13 wherein the desired state for at least one of the conditions in the set of conditions monitored by the monitoring system is a threshold angle for a pivotable back section of the patient support surface, the monitoring system is adapted to issue the alert if the pivotable back section pivots below the threshold angle, and the user interface is adapted to allow the user to customize the threshold angle.

15. The patient support apparatus of claim 13 wherein the desired state for at least one of the conditions in the set of conditions monitored by the monitoring system is a threshold height for the patient support surface, and the monitoring system is adapted to issue the alert if the patient support surface is raised above the threshold height, wherein the user interface is adapted to allow the user to customize the threshold height.

16. The patient support apparatus of claim 8 further comprising a memory onboard the patient support apparatus in which the patient-customized setting and the preset setting is stored, and wherein the user interface includes a new patient control and the controller is further configured to erase the patient-customized setting from the memory in response to user-activation of the new patient control, but retain the preset setting in the memory.

17. The patient support apparatus of claim 8
wherein the user interface further comprises an exit detection navigation control; and
the controller is further configured to, in response to user-activation of the exit detection navigation control: display an exit detection control screen on the display; determine whether an exit detection setting of the exit detection system was previously customized for the patient; and arm the exit detection system with the patient-customized exit detection setting if the exit detection setting was previously customized for the patient or with a preset exit detection setting if the exit detection setting was not previously customized for the patient.

18. The patient support apparatus of claim 8, wherein the monitoring system further comprises a plurality of sensors in communication with the controller, the plurality of sensors including at least two of the following: a side rail sensor adapted to detect a position of a siderail onboard the patient support apparatus, a head-of-bed (HOB) angle sensor adapted to detect an angle of a pivotable back section of the patient support surface, a height sensor adapted to detect a height of the patient support surface, and a bed angle sensor adapted to detect a tilt of the patient support surface.

\* \* \* \* \*